US010786459B2

(12) United States Patent
Upadhye et al.

(10) Patent No.: US 10,786,459 B2
(45) Date of Patent: Sep. 29, 2020

(54) TWIN-SCREW DRY GRANULATION FOR PRODUCING SOLID FORMULATIONS

(71) Applicants: R. P. Scherer Technologies LLC, Las Vegas, NV (US); UNIVERSITY OF MISSISSIPPI, University, MS (US)

(72) Inventors: Sampada Bhaskar Upadhye, Princeton, NJ (US); Ronald S. Vladyka, R.ph, Somerset, NJ (US); Michael Andrew Repka, Oxford, MS (US); Jun-Bom Park, Seoul (KR); Roshan Vijay Tiwari, Hillsborough, NJ (US); Hemlata Gunga Patil, Hillsborough, NJ (US); Joseph Thomas Morott, Jr., Morgantown, WV (US); Wenli Lu, Shanghai (CN)

(73) Assignees: R. P. Scherer Technologies LLC, Las Vegas, NV (US); University of Mississippi, University, MS (US)

( * ) Notice: Subject to any disclaimer, the term of this patent is extended or adjusted under 35 U.S.C. 154(b) by 32 days.

(21) Appl. No.: 15/493,568

(22) Filed: Apr. 21, 2017

(65) Prior Publication Data

US 2017/0319486 A1 Nov. 9, 2017

Related U.S. Application Data

(60) Provisional application No. 62/326,046, filed on Apr. 22, 2016.

(51) Int. Cl.
*A61K 9/16* (2006.01)
*A61K 9/00* (2006.01)
*A61K 9/20* (2006.01)
*A61K 31/4178* (2006.01)
*A61K 31/519* (2006.01)
*B01J 2/10* (2006.01)

(52) U.S. Cl.
CPC .......... *A61K 9/1682* (2013.01); *A61K 9/0053* (2013.01); *A61K 9/1635* (2013.01); *A61K 9/1641* (2013.01); *A61K 9/1647* (2013.01); *A61K 9/1652* (2013.01); *A61K 9/1694* (2013.01); *A61K 9/2054* (2013.01); *A61K 9/2095* (2013.01); *A61K 31/4178* (2013.01); *A61K 31/519* (2013.01); *B01J 2/10* (2013.01)

(58) Field of Classification Search
CPC .......... A61K 9/14; A61K 9/141; A61K 9/143; A61K 9/145; A61K 9/16; A61K 9/1605; A61K 9/01611; A61K 9/1617; A61K 9/1682; A61K 9/1688; A61K 9/1694
See application file for complete search history.

(56) References Cited

U.S. PATENT DOCUMENTS

| | | | |
|---|---|---|---|
| 3,730,663 A | 5/1973 | Hare | |
| 4,890,996 A | 1/1990 | Shimizu | |
| 5,688,510 A * | 11/1997 | Nakamichi | A61K 9/1694 424/43 |
| 6,499,984 B1 | 12/2002 | Ghebre-Sellassie et al. | |
| 7,198,803 B2 * | 4/2007 | Yasuura | A61K 9/14 424/468 |
| 8,581,134 B2 | 11/2013 | Politi et al. | |
| 8,846,088 B2 | 9/2014 | Bertelsen et al. | |
| 2004/0219220 A1 * | 11/2004 | Sherry | A61K 9/1694 424/489 |

FOREIGN PATENT DOCUMENTS

| | | |
|---|---|---|
| WO | WO 2012/160051 | 11/2012 |
| WO | WO 2016/042372 | 3/2016 |
| WO | WO-2016042372 A1 * | 3/2016 ........... A61K 9/0007 |

OTHER PUBLICATIONS

Aulton, Michael E., "Pharmaceutics: The Science of Dosage Form Design," (1988); 4 pages.
Anonymous, "The U.S. Pharmacopeia: The National Formulary," (1995) USP 23, NF 18; 2 pages.
Kleinebudde, Peter, "Roll compaction/dry granulation: pharmaceutical applications," (2004) European Journal of Pharmaceutics and Biopharmaceutics, vol. 58; 10 pages.
Van Melkebeke, Barbara et al., "Melt granulation using a twin-screw extruder: A case study," (2006) International Journal of Pharmaceutics, 326(1); 5 pages.
Rowe, Raymond C., "Handbook of Pharmaceutical Excipients," Sixth Edition, American Pharmaceuticals Association (2009); 917 pages.
Allen, Jr., Loyd V. et al., "Remington, The Science and Practice of Pharmacy," (2012) $22^{nd}$ Edition, vol. I, Gennaro, Ed., Lippincott Williams & Wilkins; 1942 pages.
Allen, Jr., Loyd V. et al., "Remington, The Science and Practice of Pharmacy," (2012) $22^{nd}$ Edition, vol. II, Gennaro, Ed., Lippincott Williams & Wilkins: 1005 pages.
Weatherley, Sharleen et al., "Hot-Melt Granulation in a Twin Screw Extruder: Effects of Processing on Formulations with Caffeine and Ibuprofen," (2013) Journal of Pharmaceutical Sciences, vol. 102; 7 pages.

(Continued)

*Primary Examiner* — Micah Paul Young
(74) *Attorney, Agent, or Firm* — Morrison & Foerster LLP

(57) ABSTRACT

A dry granulation process using a twin-screw extruder for granulating a powder mixture which includes at least one active ingredient and at least one carrier. The process includes steps of kneading the powder mixture in the screw barrel of the twin-screw extruder at a barrel temperature below a melting point of the at least one active ingredient and a melting point or a glass transition temperature of the at least one carrier to provide a kneaded powder mixture, and extruding the kneaded powder mixture to form granules. Granules and tablets produced using the dry granulation process in the twin-screw extruder are also provided.

30 Claims, 22 Drawing Sheets

(56) References Cited

OTHER PUBLICATIONS

Maniruzzaman, Mohammed et al., "Continuous twin-screw granulation for enhancing the dissolution of poorly water soluble drug," (2015) International Journal of Pharmaceutics 496; 11 pages.

Thompson, M.R. et al., (2016) "Heat Activated Dry Granulation Within the Twin Screw Granulator," SPE ANTEC, Indianapolis; 6 pages.

International Search Report and Written Opinion dated Jul. 7, 2017, directed to International Application No. PCT/2017/028955; 13 pages.

Desai et al. (Mar. 2013). "Melt Granulation: An Alternative to Traditional Granulation Techniques," Indian Drugs 50(3): 5-13.

Monteyne et al. (Oct. 2016). "Stearic Acid and High Molecular Weight PEO as Matrix for the Highly Water Soluble Metoprolol Tartrate in Continuous Twin-Screw Melt Granulation," International Journal of Pharmaceutics 512(1): 158-167.

Vaingankar et al. (Jan. 2017). "Continuous Melt Granulation to Develop High Drug Loaded Sustained Release Tablet of Metformin HCl," Asian Journal of Pharmaceutical Sciences 12: 37-50.

* cited by examiner

TWIN-SCREW DRY GRANULATION FOR PRODUCING SOLID FORMULATIONS

REFERENCE TO RELATED APPLICATIONS

This application claims the priority of U.S. Provisional Application No. 62/326,046 filed Apr. 22, 2016, the entire contents of which are incorporated herein by reference.

BACKGROUND OF THE DISCLOSURE

1. Field of the Disclosure

The present disclosure relates to a granulation process for producing solid formulations. In particular, the present disclosure relates to a dry granulation process using one or more twin-screw extruders for producing solid, high-dose formulations or formulations of dehydration sensitive ingredients.

2. Description of the Related Technology

Granulation is a process in which small particles agglomerate into larger, multi-particle masses called granules. The granulation process is routinely utilized in the pharmaceutical industry for formulating solid oral dosage formulations as well as in various other industries. Granulation has several advantages such as reducing dust of fine particles that may cause potential health and environmental hazards, avoiding segregation of different components in a formulation, producing granules that are easy to handle and transport, and improving flowability and compressibility of the ingredients.

Granulation processes can be divided into two types: wet granulation and dry granulation. Wet granulation processes utilize some form of solvent or liquid binder to bind small particles together to form agglomerates. Dry granulation processes are carried out without a solvent or liquid binder. Wet granulation may use any of low-shear mixing, high-shear mixing, extrusion-spheronization, or fluid-bed processing for producing wet granules, which are then dried, sieved, and optionally ground prior to being compressed into tablets (when tableting is desired). Wet granulation is frequently used in the pharmaceutical industry, but it has proven to have some disadvantages. In some cases, for example, the solvent or liquid binder may have an adverse effect on other ingredients in the formulation and/or on one or more properties of the end product, such as a tablet. Further, the wet granulation process usually requires a drying step to remove the solvent or liquid binder after granulation.

WO 2012160051 A2 discloses wet granulation methods using different granulation solvents such as isopropyl alcohol, dichloromethane, methanol, acetone or mixtures thereof for manufacturing cetyl myristate or cetyl palmitate or a combination of cetyl myristate and cetyl palmitate. Moreover, it is known that selection of an appropriate granulation solvent in an appropriate amount is important for granulation of waxy materials. The physical and chemical properties of the active ingredient(s) also should be considered for the selection of the granulation method.

Dry granulation can be employed to overcome some of the disadvantages of wet granulation that result from the use of a solvent or liquid binder. In a dry granulation process, powdered components, typically in the form of fine particles are mixed prior to granulation and then compressed to yield hard granules which may then be ground and sieved, as necessary, to produce particles of a desired size distribution. In some cases, dry granulation may use either slugging or roller compression to produce compacts, also known as briquettes, flakes or ribbons, which may then be milled to obtain the desired granules. Unfortunately, it is often challenging to produce granules having the desired properties using dry granulation. Dry granulation processes, as well as known issues related to them, are discussed in a review article by Peter Kleinebudde, "Roll compaction/dry granulation: pharmaceutical applications," *European Journal of Pharmaceutics and Biopharmaceutics*, vol. 58, pages 317-326, (2004).

Roller compaction is a widely used dry granulation method as it does not require an additional drying step. This enables robust processes using small equipment. Agglomeration depends mainly on the compactability of the substances, thus high amounts of fines are often produced, which is the major drawback of the roller compaction process. If a tablet press is used for the compaction process, the process is termed, "slugging." However, since particles with a small particle size do not flow well into the die of a tablet press, this may result in weight differences from one tablet (slug) to another. This, in turn, causes large fluctuations in the forces applied to the individual slugs, which translates into variations in the mechanical strength of different slugs. Therefore, the properties of granulates obtained by milling the slugs also may not be controlled to the desired extent. This is one of the main reasons why slugging is infrequently used as a dry granulation method.

US 2010/0184861 discloses a method for producing granules from a powder, by application of a compaction force on the powder to produce granules comprising a mixture of fine particles, followed by separating and removing fine particles and/or small granules from larger granules by entraining the fine particles and/or small granules in a gas stream. The powder, which may comprise APIs and/or pharmaceutically acceptable carriers, is generally composed of fine particles with a mean particle size of less than 100, 50, or 20 µm. The method may be carried out as a continuous process in the substantial absence of liquid.

U.S. Pat. No. 8,846,088 discloses a melt granulation process for making a composition comprising a powder of a calcium-containing compound and a sugar alcohol. The process is said to produce granules with a desirable taste and mouth feel. Heating is applied to the composition during granulation to sufficiently melt or soften the sugar alcohol to enable at least partial coverage of the calcium-containing compound particles. The sugar alcohol provides taste masking of the calcium-containing compound and can also improve mouth feel. The method is especially suitable for manufacturing tablets having a high loading of a calcium-containing compound.

U.S. Pat. No. 6,499,984 discloses a single pass, continuous, automated system for producing pharmaceutical granules using a wet granulation process. The system includes multiple feeders to feed powders and liquids into the system, a twin-screw processor to granulate the powders, a radio frequency or microwave based drying apparatus to dry the granules, and at least one mill to process the dried granules to desired particle sizes. The system also includes means for monitoring key process parameters on-line, which parameters may be controlled by a controller that provides feedback control to the monitored components in the system. The produced granules can be compressed into tablets or incorporated as a fill material into capsules. The system produces granules having consistent properties even when production is scaled-up for commercial manufacture.

It is known in the art to use twin-screw extruders for granulation using a wet granulation process. In a twin-screw extruder, the input materials, typically powders and granulation fluid, are introduced into a screw barrel by a feeder and granules are produced, often by extrusion of the wet mass through a die block, at the exit of the twin-screw extruder. Maniruzzarnan can be prepared by wet granulations of ibuprofen using hot-melt twin screw extruder using water as a liquid binder. (Maniruzzaman M, Nair A, Renault M, Nandi U, Scoutaris N, Famish R, Bradley M S, Snowden M J, Douroumis D. Continuous twin-screw granulation for enhancing the dissolution of poorly water soluble drug. International journal of pharmaceutics. 2015 Dec. 30:496 (1):52-62).

It is also known in the art to use twin-screw extruders for melt granulation. (see e.g. Michael R. Thompson "Hot-Melt Granulation in a Twin Screw Extruder: Effects of Processing on Formulations with Caffeine and Ibuprofen" Journal of Pharmaceutical Sciences, Vol. 102, 4330-4336 (2013); and Van Melkebeke et al., "Melt granulation using a twin-screw extruder: a case study." International Journal of Pharmaceutics, 2006 Dec. 1; 326(1), pp. 89-93) investigated the use of a twin screw extruder for melt granulation. Polyethylene glycols (PEG 400 and 4000) were used as meltable binders. During granulation the drug particles were finely dispersed in the molten mixture, whereby the PEG 400 and 4000 created a micro-environment around the drug particles enhancing the dissolution rate.

SUMMARY

The present disclosure is directed to a dry granulation process using a twin-screw extruder. Extrusion using a twin-screw extruder may provide advantages such as economical processing, a small scale-up footprint, reduced in-process times, and reduced processing steps with continuous operation. Although it was known in the art to make granules using twin-screw extruders using a wet granulation process or a melt granulation process, Applicants have developed the use of a twin-screw extruder to make granules by a dry granulation process.

The dry granulation process of the present disclosure can be performed without solvent or liquid binders. The dry granulation process of the disclosure can facilitate the handling of sensitive ingredients that may be subject to dehydration or adversely affected by solvents, excessive heat, or liquid binders. In some cases, the present disclosure can also facilitate the production of high loading granules.

In some embodiments, a method of producing granules includes mixing a first powder including at least one active ingredient and a second powder including at least one carrier to form a powder mixture; feeding the powder mixture to a twin-screw extruder without a solvent or a liquid binder; kneading the powder mixture in a heated screw barrel of the twin-screw extruder, wherein all temperatures along a length of the screw barrel are below the melting point of the at least one active ingredient and below the melting point or a glass transition temperature of the at least one carrier to form a kneaded powder mixture; and extruding the kneaded powder mixture to form the granules. In some embodiments, the twin-screw extruder includes two screws that are fully intermeshing, co-rotating screws. In some embodiments, a barrel temperature at one location along a length of the screw barrel is different from a barrel temperature at another location along the length of the screw barrel. In some embodiments, a first zone closest to an outlet of the screw barrel has a lower barrel temperature than a second zone at a center portion along the length of the screw barrel. In some embodiments, all temperatures along the length of the screw barrel are between 50-100° C. In some embodiments, the twin-screw extruder does not have a die block for extruding the granules. In some embodiments, the powder mixture further comprises a lubricant. In some embodiments, the lubricant is added to the powder mixture before kneading the powder mixture. In some embodiments, the powder mixture includes 0.01-1 wt % the powder mixture. In some embodiments, the lubricant is selected from the group consisting of magnesium stearate, zinc stearate, lithium stearate, calcium stearate, aluminum stearate, sodium stearyl fumarate, talc, glyceryl behenate, and colloidal silicon dioxide. In some embodiments, all temperatures along the length of the screw barrel are below the melting point or the glass transition temperature of all components in the powder mixture. In some embodiments, the melting point or the glass transition temperature of the at least one carrier is lower than the melting point of the at least one active ingredient. In some embodiments, the powder mixture includes two or more polymeric carriers. In some embodiments, the powder mixture further includes at least one of a plasticizer, binder, filler, disintegrant, or organic acid. In some embodiments, the powder mixture further includes an organic acid. In some embodiments, a screw speed of the twin-screw extruder is less than 200 rpm. In some embodiments, a feed rate into the twin-screw extruder is less than about 400 g/hr. In some embodiments, the method includes pressing the granules into a tablet. In some embodiments, the tablet has a hardness of 5-20 kp. In some embodiments, the tablet has a friability of less than 0.5%.

In some embodiments, a granule is produced by a method including mixing a first powder including at least one active ingredient and a second powder including at least one carrier to form a powder mixture; feeding the powder mixture to a twin-screw extruder without a solvent or a liquid binder; kneading the powder mixture in a heated screw barrel of the twin-screw extruder, wherein all temperatures along a length of the screw barrel are below the melting point of the at least one active ingredient and below the melting point or the glass transition temperature of the at least one carrier to form a kneaded powder mixture; and extruding the kneaded powder mixture to form the granule. In some embodiments, a granule includes at least one active ingredient and at least one carrier having a melting point or a glass transition temperature lower than the melting point of the at least one active ingredient, wherein the granule has a compressibility index of 10-30 and a Hausner ratio of less than 1.25.

In some embodiments, the at least one active ingredient is selected from the group consisting of heat-sensitive active pharmaceutical ingredients, dehydration-sensitive active pharmaceutical ingredients, poorly-compressible active pharmaceutical ingredients, and high-dosage active pharmaceutical ingredients. In some embodiments, the at least one carrier is selected from the group consisting of polysaccharides, povidones, acrylates, celluloses and polyols. In some embodiments, the at least one carrier is selected from the group consisting of homopolymers and copolymers of N-vinyl pyrrolidone, copolymers of N-vinyl pyrrolidone and vinyl acetate or vinyl propionate; cellulose esters and cellulose ethers, hydroxyalkylcelluloses, hydroxyalkylalkylcelluloses, cellulose phthalates, cellulose succinates; polyethylene oxide, polypropylene oxide, copolymers of ethylene oxide and propylene oxide; polyacrylates, polymethacrylates, polyacrylamides; vinyl acetate polymers, polyvinyl alcohol, oligo- and polysaccharidesand mixtures of one or more thereof. In some embodiments, the at least one carrier is selected from the group consisting of hydroxylpropylcellulose, ethylcellulose, carboxymethylcellulose, hydroxyethylcellulose, methylcellulose, ethylhydroxyethylcellulose, hydroxyethylmethylcellulose, hydrophobically modified hydroxyethylcellulose, hydrophobically modified ethylhydroxyethylcellulose, carboxymethylhydroxyethylcellulose, and carboxymethyl hydrophobically modified hydroxyethylcellulose. In some embodiments, the at least one carrier is a polymeric carrier having a molecular weight in a range of 2,000-2,000,000 Daltons.

In some embodiments, the granules have an angle of repose of less than or equal to 30. In some embodiments, the granules have a compressibility index of 10-30. In some embodiments, the granules have a Hausner ratio of less than 1.25. In some embodiments, the granules have a true density of 1.15-1.35. In some embodiments, the granules have a surface area of 0.05-0.45. In some embodiments, an oral dosage formulation includes at least one granule, wherein the oral dosage formulation is a capsule, pellet, sachet, powder, or tablet.

In one aspect, the present invention provides a dry granulation process using a twin-screw extruder for granulating a powder mixture which includes at least one active ingredient and a carrier. The dry granulation process includes the steps of kneading the powder mixture in the screw barrel of the twin-screw extruder under conditions that maintain the barrel temperature below the melting point of the at least one active ingredient as well as below the melting point or the glass transition temperature of all of the components contained in the powder mixture to provide a kneaded powder mixture, and extruding the kneaded powder mixture to form granules.

In another aspect, the screw barrel has plurality of zones spaced along the length of the screw barrel and at least one of the zones has a barrel temperature that is different from the barrel temperature of one or more other zones.

In yet another aspect, a powder lubricant is added to the powder mixture prior to the kneading step. In one embodiment, the powder lubricant may be selected from magnesium stearate, zinc stearate, lithium stearate, calcium stearate, aluminum stearate, sodium stearyl fumarate, talc, glyceryl behenate and colloidal silicon dioxide.

In yet another aspect, the least one active ingredient is selected from heat-sensitive ingredients, dehydration-sensitive ingredients, poorly-compressible ingredients, high-dosage ingredients and ingredients that require high-drug loading.

In yet another aspect, the powder mixture includes one or more additional components selected from plasticizers, non-polymeric carriers, binders, fillers and disintegrants.

In yet another aspect, granules are provided using the dry granulation process of the invention in the twin-screw extruder. Also provided are tablets made from the granules produced by the granulation process of the invention.

Reference to "about" a value or parameter herein includes (and describes) variations that are directed to that value or parameter per se. For example, description referring to "about X" includes description of "X". As used herein, the singular forms "a," "an," and "the" are intended to include the plural forms as well, unless the context clearly indicates otherwise. It is also to be understood that the term "and/or" as used herein refers to and encompasses any and all possible combinations of one or more of the associated listed items. It is further to be understood that the terms "includes," "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Additional advantages will be readily apparent to those skilled in the art from the following detailed description. The examples and descriptions herein are to be regarded as illustrative in nature and not restrictive.

DETAILED DESCRIPTION

Figure 1:
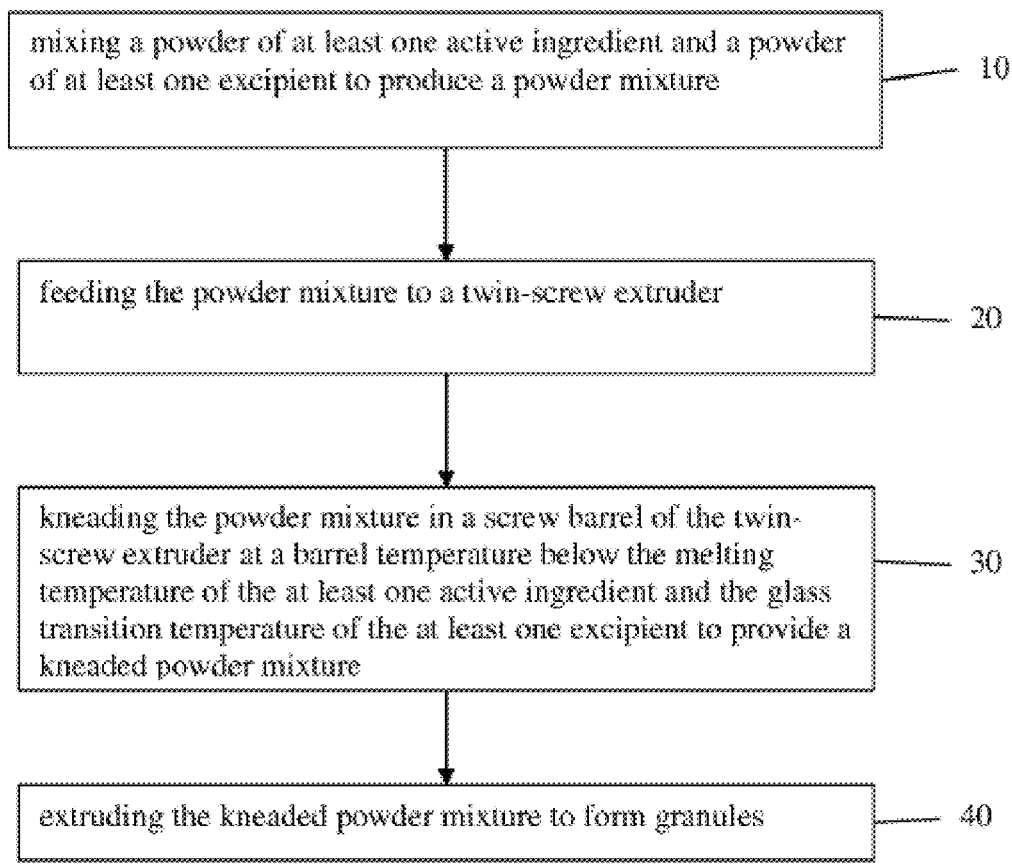
FIG. 1 is a flow chart illustrating a dry granulation process according to one embodiment of the present disclosure.

Although it was known in the art to make granules using twin-screw extruders using a wet granulation process or a melt granulation process, Applicants have developed the use of a twin-screw extruder to make granules by a dry granulation process. As such, the dry granulation process of the present disclosure can be performed without solvent or liquid binders and can facilitate the handling of sensitive ingredients that may be subject to dehydration or adversely affected by solvents, excessive heat, or liquid binders. In addition, the present disclosure can also facilitate the production of high loading granules.

For illustrative purposes, the principles of the present disclosure are described by referencing various exemplary embodiments. Although certain embodiments of the disclosure are specifically described herein, one of ordinary skill in the art will readily recognize that the same principles are equally applicable to, and can be employed in, other systems and methods. Before explaining the disclosed embodiments of the present disclosure in detail, it is to be understood that the disclosure is not limited in its application to the details of any particular embodiment shown. Additionally, the terminology used herein is for the purpose of description and not for limitation. Furthermore, although certain methods are described with reference to steps that are presented herein in a certain order, in many instances, these steps can be performed in any order as may be appreciated by one skilled in the art; the method is therefore not limited to the particular arrangement of steps disclosed herein.

As used herein, the term "pharmaceutically acceptable" refers to those compounds, materials, and/or compositions which are, within the scope of sound medical judgment, suitable for contact with the tissues of mammals, especially humans, without excessive toxicity, irritation, allergic response and other problematic complications commensurate with a reasonable benefit/risk ratio.

As used herein, the term "active pharmaceutical ingredient" or API means any compound, substance, drug, medicament, or active ingredient having a therapeutic or pharmacological effect, and which is suitable for administration to a mammal, e.g., a human, in a composition that is particularly suitable for oral administration.

As used herein, the term "poorly compressible" refers to a compound, composition or granule that does not easily bond to form a tablet upon the application of a force. A tablet that is poorly compressible would have a weight loss of greater than about 1 weight % when tested for friability as described in the U.S. Pharmacopeias/National Formulary (USP 23/NF 18, pp 1981). Poorly compressible compounds, compositions or granules may require additional processing and special formulation methods, for example wet granulation or roller compacting. High levels of some active ingredients in the granules may also render the composition unsuitable for direct compression because of one or both of the poor flowability and poor compressibility of such granules.

As used herein, the term "extended release" refers to the gradual but continuous release of the active ingredient content from a solid formulation over a relatively extended period. The release may continue through until and after the dosage formulation reaches the intestine.

As used herein, "delayed release" refers to the release of an active ingredient which does not start immediately when the formulation reaches the stomach but is delayed for a period of time, for instance, until when the dosage formulation reaches the intestine such that the increasing pH can be used to trigger release of the active ingredient from the formulation.

In one aspect, the present disclosure provides a dry granulation process for making a granular formulation using a twin-screw extruder. In some embodiments, two or more twin-screw extruders may be employed in the same manner as the twin-screw extruder described herein. In one embodiment, the dry granulation process may include one or more of the steps of mixing a powder of at least one active ingredient and a powder of at least one carrier to produce a powder mixture, feeding the powder mixture to a twin-screw extruder having a screw barrel that is heated to a barrel temperature below the melting point of the at least one active ingredient and the melting point or the glass transition temperature of all of the components of the powder mixture including the carrier, kneading the powder mixture in the screw barrel to form a kneaded powder mixture and extruding the kneaded powder mixture to form granules.

Several granulation parameters may be important for dry granulation of a particular powder mixture. These parameters can include the screw design used in the twin-screw extruder, feed rate of the powder mixture to the screw barrel of the twin-screw extruder, the residence time of the powder mixture in the screw barrel of the twin-screw extruder, and the barrel temperature and/or temperature profile of the screw barrel of the twin-screw extruder. These parameters function can be employed to ensure that the powder mixture is subjected to the conditions required for the powder to agglomerate and form granules.

One goal of the dry granulation process may be to ensure substantially consistent heating of the powder mixture in the screw barrel of the twin-screw extruder to avoid localized melting of the active ingredient and/or carrier. Another goal of the dry granulation process may be to subject the powder mixture to sufficient mechanical shear exerted by the rotating screws of the twin-screw extruder to cause agglomeration of the powder into granules without melting one or more components of the powder mixture.

In one aspect, the present disclosure provides a Quality by Design approach in determining the granulation parameters for extruding granules made from a particular powder mixture of an active ingredient and a carrier. The Quality by Design approach may be performed by varying one or more of the granulation parameters and/or the input composition while monitoring the quality of the final product, which may be the granules and/or tablets made from the granules. The quality of the granules may be determined by observing the granules by scanning electronic microscopy and measuring one or more of the properties of the granules including, for example, the bulk density, the hardness, the friability, and weight variation. Similar properties of tablets made from the granules may also be measured. In addition, in some embodiments, the crystal structure of the active ingredient is preferably preserved in the granules as well as in tablets made therefrom. The crystal structure of the active ingredient may be determined by Fourier Transform Infrared Spectroscopy. The Quality by Design approach is further illustrated by the Examples of the present application.

The twin-screw extruder used in the dry granulation process employs two screws located in a single screw barrel for kneading and extruding the powder mixture. Typically, the screw barrel is provided with a feeder at an inlet and an outlet, preferably with a die block. In a typical process as depicted in FIG. 1, a powder mixture can be formed in mixing step 10 and fed 20 to the screw barrel by the feeder. Granules can be produced by a combination of kneading 30 the powder mixture in the screw barrel and extruding 40 the powder mixture through a die located at the outlet. Rotation of the twin screws can propel the powder mixture in the screw barrel from the inlet to the outlet, as well as kneading 30 the powder mixture. Examples of twin-screw extruders include, for example, in U.S. Pat. Nos. 4,890,996 and 3,730,663, as well as in Aulton, Pharmaceutics, the Science of Dosage Form Design, (1988) 623-625, the disclosures of which are hereby incorporated herein by reference in their entirety.

The dry granulation process may be conducted as a continuous solvent-free process, in which the powder mixture is continuously introduced into the screw barrel and the granules are continuously extruded 40, optionally through a die block from the outlet of the screw barrel. In some embodiments, the twin-screw extruder may be used in the process without the die block in order to prevent over-densification of material inside the screw barrel.

Two features of the twin-screw extruder used in the present disclosure that may influence the results of the granulation process are the meshing characteristics and type of rotation of the twin screws. The twin screws of the twin-screw extruder may be fully intermeshing, partially intermeshing, or non-intermeshing. The twin screws of the twin-screw extruder may rotate in opposite directions (counter-rotation) to form a single stream of powder mixture that travels between the screws. The twin screws may alternatively rotate in the same direction (co-rotation) which forms two streams of powder mixture that travel in parallel along two screws. In one embodiment, the twin-screw extruder employs co-rotating twin-screws that are fully intermeshing.

The granulation process can be operated under the condition that the screw barrel of the twin-screw extruder has a barrel temperature that is below the melting point of the active ingredient and the melting point or glass transition temperature of all of the components of the powder mixture including the carrier. In some embodiments, the barrel temperature of the screw barrel is substantially uniform along the length of the screw barrel. In some other embodiments, the barrel temperature of the screw barrel may vary along the length of the screw barrel. In such embodiments, there may be a plurality of zones along the length of the screw barrel, each with a barrel temperature that may be different from the barrel temperature of one or more other zones. In various embodiments, there may be from 5 to 12 zones or from 7 to 10 zones in the screw barrel (see Table 1 for example). The barrel temperatures of all of the zones can be below the melting point of the active ingredient and the melting point or the glass transition temperature of all of the components of the powder mixture including the carrier.

In one embodiment, a zone adjacent to the inlet (feed zone) and a zone at a central portion of the screw barrel between the inlet and outlet each have a barrel temperature higher than the barrel temperature of a zone adjacent to the outlet of the screw barrel (outlet zone or die zone). In another embodiment, the zone at the central portion of the screw barrel has a barrel temperature that is higher than the barrel temperatures of the zones adjacent to the inlet and outlet of the screw barrel. In yet another embodiment, the barrel temperatures of the zones adjacent to the inlet and outlet of the screw barrel are substantially the same, and are lower than the barrel temperature at the zone at the central portion of the screw barrel. Some exemplary configurations of the barrel temperatures of the screw barrel are represented in Table 1 below.

TABLE 1

Barrel temperatures in the Screw Barrel of the Twin-Screw Extruder
Barrel Temperature (° C.)

| Feed Zone | Zone 2 | Zone 3 | Zone 4 | Zone 5 | Zone 6 | Zone 7 | Zone 8 | Die |
|---|---|---|---|---|---|---|---|---|
| N/A | High | High | High | High | High | Low | Low | Low |
| N/A | Low | Low | High | High | High | Low | Low | Low |

In some embodiments, each barrel temperature of the screw barrel is below the melting point of the active pharmaceutical ingredient and the melting point or glass transition temperature of the polymeric carrier by about 15° C., or about 20° C., or about 25° C., or about 30° C., or about 35° C., or about 40° C., or about 45° C. Each barrel temperature of the screw barrel is generally in the range of from about 50° C. to about 100° C., or from about 50° C. to about 95° C., or from about 55° C. to about 95° C., or from about 55° C. to about 90° C., or from about 60° C. to about 90° C., or from about 60° C. to about 85° C., or from about 65° C. to about 85° C., or from about 65° C. to about 80° C., or from about 70° C. to about 80° C.

In some embodiments, screw barrel is heated to the one or more barrel temperatures in order to transfer heat to the powder mixture therein. In some embodiments, one or more components of the mixture may be preheated before being fed 20 to the inlet of the twin-screw barrel but care should be taken to avoid agglomeration if preheating. The powder mixture may be preheated to a temperature of about 20° C., or about 15° C., or about 10° C. below a barrel temperature of the screw barrel.

The twin screws of the extruder can knead 30 the powder mixture and preferably ensure substantially even heating of the powder mixture by the screw barrel by moving the powder mixture in a certain manner. The twin screws can also be employed to impart shearing mechanical energy to the powder mixture. In the dry granulation process, the thermal energy transferred to the powder mixture from the barrel and the shearing mechanical energy imparted to the powder mixture by the rotating twin screws can combine to cause granulation of the powder mixture. The screw design may be varied to control the dry granulation process because variation of the number of mixing elements within a defined length of the screw can be used to vary the amount of shearing mechanical energy applied to the powder mixture.

The twin screws also can function to move the powder mixture from the inlet of the screw barrel to the outlet of the screw barrel at a speed that determines the residence time of the powder mixture in the screw barrel. The feed rate of the powder mixture to the screw barrel can also be a factor that contributes to determination of the residence time of the powder mixture in the screw barrel. Sufficient residence time in the screw barrel can allow the powder mixture to absorb sufficient heat and to be exposed to sufficient shear energy to ensure agglomeration of the powder mixture into granules having sufficient hardness and friability to provide useful products.

Figure 2A:
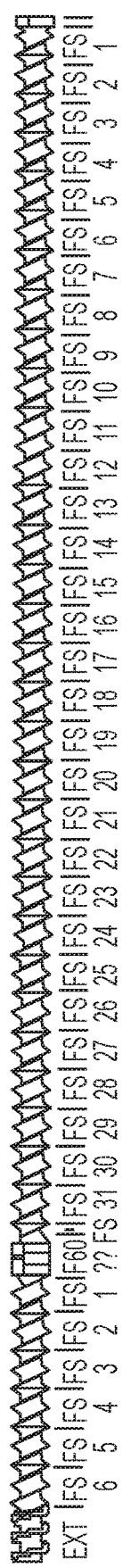
FIGS. 2A-2E illustrate various screw designs that may be used in the twin-screw extruder used to carry out the dry granulation process of the present disclosure.
Figure 2B:
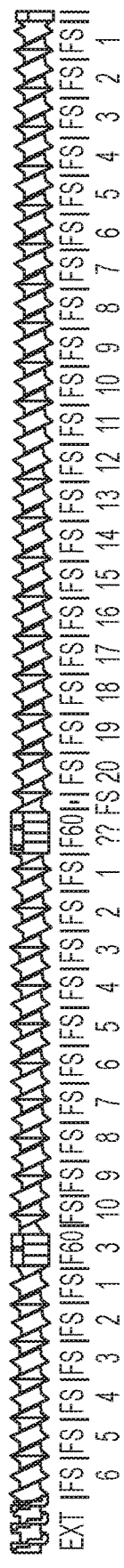
Figure 2C:
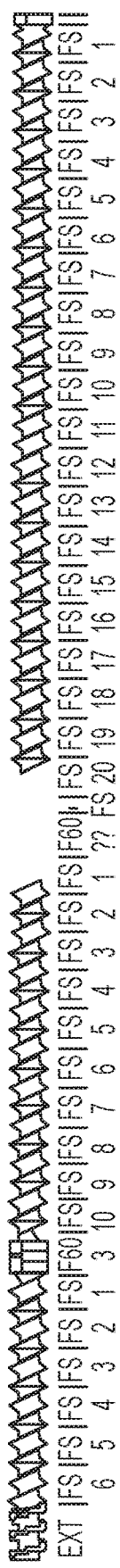
Figure 2D:
Figure 2E:
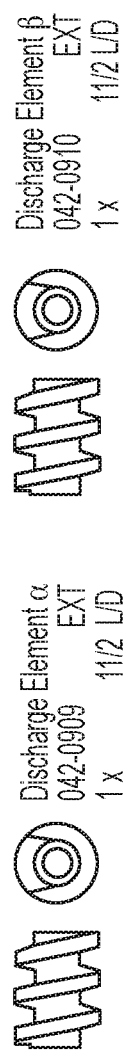

Various screw designs used in twin-screw extruders are shown in FIGS. 2A-2E. More specifically, FIG. 2A shows a screw design that is similar to those used in polymer processing or hot melt extrusion operations. Such a screw design can employ numerous mixing elements to impart considerable shear energy to the powder mixture within the barrel during the kneading step 30. The screw design of FIG. 2B consists of conveying elements but no mixing elements, and thus can serve to pump the powder mixture through the screw barrel without imparting significant shear energy thereto. The screw design shown in FIG. 2C is similar to the screw design of FIG. 2B, except that three mixing elements are added proximate to the discharge section of the screws that is positioned at the outlet of the screw barrel. The design of FIG. 2C is capable of yielding granules, indicating that this screw design can impart a sufficient amount of shear energy to the powder mixture for granulation to occur when employed in combination with a heated barrel. Two additional screw designs capable of producing granules are shown in FIGS. 2D-2E. In FIG. 2D, the screw is similar to the screw of FIG. 2C except that it has an additional mixing element near the feed zone. The screw design in FIG. 2E is a modified version of the screw design of FIG. 2D wherein the offset angle of the mixing elements proximate to the discharge section of the screw have been altered.

In certain embodiments, a back pressure in the screw barrel may be required to facilitate agglomeration of the powder mixture. This back pressure may be achieved by using the twin screws to force the powder mixture in the screw barrel through a die block or an outlet that is narrower than an adjacent portion of the screw barrel. Such a back pressure is normally not required for agglomeration in hot melt extrusion processes because agglomerated material typically appears immediately when the carrier becomes molten. Further, in a melt granulation process, torque values tend to be steadily elevated up to approximately 5.3 Nm as the carrier becomes more viscous in the melt material. In contrast, during the dry granulation process of the present disclosure, the torque values remain significantly lower with relatively large fluctuations ranging from about 0.72-3.12 Nm.

The powder mixture in the screw barrel can undergo agglomeration and forms granules, which may then be extruded 40, optionally through a die block, to produce granules. In certain embodiments, the granules may be used to make oral dosage forms such as capsules or tablets.

As will be appreciated by a person skilled in the art, given a particular powder mixture comprising an active ingredient and an carrier, the particular granulation parameters for the twin-screw dry granulation process of the disclosure, including at least the screw design, feed rate, screw barrel temperature, screw barrel temperature profile and residence time may be determined by use of the present disclosure in combination with the "Quality by Design" approach with the goal of obtaining desired granules. It is understood that these parameter are dependent on each other and also on the composition of the powder mixture, since different active ingredients and carriers may require different feed rates, barrel temperatures, barrel temperature profiles, residence times, and/or screw designs for producing the desired granules. In some embodiments, one or more characteristics of the granules may be used to determine the granulation parameters. These characteristics include one or more of the preservation of the crystalline lattice of a crystalline active ingredient, granule surface morphology, phase changes of the active ingredient, chemical interactions, firmness, friability, the compressibility index, the angle of repose, the Hausner ratio, and any other relevant property of the granules.

In some embodiments, the angle of repose of the granules can be less than about 50, less than about 45, less than about 40, less than about 35, or less than or equal to about 30. In some embodiments, the angle of repose of the granules can be about 15-50, about 20-45, about 25-40, about 25-35, or about 25-30.

In some embodiments, the (Carr's) compressibility index is less than about 30, less than about 25, less than about 20, or less than about 15. In some embodiments, the (Carr's) compressibility index of the granules is about 1-40, about 4-30, about 10-30, about 15-25, or about 19-21. In some embodiments, the Hausner ratio of the granules can be less than about 1.5, less than about 1.4, less than about 1.3, or less than about 1.25. In some embodiments, the Hausner ratio of the granules can be about 1-1.35, about 1-1.3, about 1-1.25, or about 1-1.2.

In some embodiments, the true density of the granules is about 1.1-1.4, about 1.15-1.35, or about 1.2-1.3. In some embodiments, the surface area of the granules is about 0.01-0.5, about 0.05-0.45, or about 0.1-0.4. In some embodiments, the percentage of fines (particles with a size less than 500 µm) of the granules produced is less than about 50%, less than about 40%, less than about 30%, less than about 20%, less than about 15%, less than about 10%, less than about 8%, less than about 7%, less than about 6%, less than about 5%, less than about 4%, or less than about 3%.

Further, the suitability of the granules for the production of tablets or other solid formulations with desired properties can also be evaluated and employed for the purpose of determining suitable granulation parameters. For, example, in the case of tablets or other solid formulations, properties such as the ability to provide a high loading of active ingredient, storage stability, hardness, friability, and extended or delayed release properties may also be used for the purpose of determining one or more of the granulation parameters.

In some embodiments, a tablet or other solid formulation produced from the granules disclosed herein has a hardness of about 1-20 kp, about 5-20 kp, about 8-20 kp, or about 10-20 kp. In some embodiments, a tablet or other solid formulation produced from the granules disclosed herein has a friability of about 0-0.5%, about 0-0.4%, about 0-0.3%, about 0-0.2%, about 0-0.1%, or about 0-0.05%.

The present disclosure surprisingly found that without having to add a solvent, a liquid binder to the powder mixture, and without having to melt a component of the powder mixture, the dry granulation process of the disclosure when carried out in an appropriate twin-screw extruder can provide acceptable granules with desired properties. This dry granulation process can greatly simplify the formulation of many active ingredients since this process does not require high temperatures, solvents or liquid binders, and/or subsequent drying operations.

The active ingredients that may be used in the dry granulation process of the present disclosure may include active pharmaceutical ingredients, vitamins, minerals, and nutritional components. In particular, active pharmaceutical ingredients for which the present dry granulation process may be used include, but are not limited to antacids, anti-inflammatory substances, coronary dilators, cerebral dilators, peripheral vasodilators, anti-infectives, psychotropics, antimanics, stimulants, antihistamines, anti-cancer therapeutic compounds, laxatives, decongestants, vitamins, gastrointestinal sedatives, antidiarrheal preparations, anti-anginal therapeutic compounds, vasodilators, antiarrythmics, antihypertensive therapeutic compounds, vasoconstrictors and migraine treatments, anticoagulants and antithrombotic therapeutic compounds, analgesics, antipyretics, hypnotics, sedatives, anti-emetics, anti-nauseants, anti-convulsants, neuromuscular therapeutic compounds, hyper- and hypoglycemic agents, thyroid and antithyroid preparations, diuretics, anti-spasmodics, uterine relaxants, mineral and nutritional additives, anti-obesity therapeutic compounds, anabolic therapeutic compounds, erythropoietic therapeutic compounds, anti-asthmatics, expectorants, cough suppressants, mucolytics, anti-uricemic therapeutic compounds, and therapeutic compounds or substances acting locally in the mouth.

Exemplary active pharmaceutical ingredients that may be used in the dry granulation process of the disclosure include, but are not limited to, gastrointestinal sedatives, such as metoclopramide and propantheline bromide; antacids, such as aluminum trisilicate, aluminum hydroxide and cimetidine; anti-inflammatory therapeutic compounds, such as phenylbutazone, indomethacin, naproxen, ibuprofen, flurbiprofen, diclofenac, dexamethasone, prednisone and prednisolone; coronary vasodilator therapeutic compounds, such as glyceryl trinitrate, isosorbide dinitrate and pentaerythritol tetranitrate; peripheral and cerebral vasodilators, such as soloctidilum, vincamine, naftidrofuryl oxalate, co-dergocrine mesylate, cyclandelate, papaverine and nicotinic acid; anti-infective therapeutic compounds, such as erythromycin stearate, cephalexin, nalidixic acid, tetracycline hydrochloride, ampicillin, flucolaxacillin sodium, hexamine mandelate and hexamine hippurate; neuroleptic therapeutic compounds, such as fluazepam, diazepam, temazepam, amitryptyline, doxepin, lithium carbonate, lithium sulfate, chlorpromazine, thioridazine, trifluperazine, fluphenazine, piperothiazine, haloperidol, maprotiline hydrochloride, imipramine and desmethylimipramine; central nervous stimulants, such as methylphenidate, ephedrine, epinephrine, isoproterenol, amphetamine sulfate and amphetamine hydrochloride; anti-histamic therapeutic compounds such as diphenhydramine, diphenylpyraline, chlorpheniramine and brompheniramine; anti-diarrheal therapeutic compounds, such as bisacodyl and magnesium hydroxide; laxative therapeutic compounds, such as dioctyl sodium sulfosuccinate; nutritional supplements, such as ascorbic acid, alpha tocopherol, thiamine and pyridoxine; anti-spasmotic therapeutic compounds, such as dicyclomine and diphenoxylate; therapeutic compounds effecting the rhythm of the heart, such as verapamil, nifedepine, diltiazem, procainamide, disopyramide, bretylium tosylate, quinidine sulfate and quinidine gluconate; therapeutic compounds used in the treatment of hypertension, such as propranolol hydrochloride, guanethidine monosulphate, methyldopa, oxprenolol hydrochloride, captopril and hydralazine; therapeutic compounds used in the treatment of migraine, such as ergotamine; therapeutic compounds effecting coagulation of blood, such as epsilon aminocaproic acid and protamine sulfate; analgesic therapeutic compounds, such as acetylsalicylic acid, acetaminophen, codeine phosphate, codeine sulfate, oxycodone, dihydrocodeine tartrate, oxycodeinone, morphine, heroin, nalbuphine, butorphanol tartrate, pentazocine hydrochloride, cyclazacine, pethidine, buprenorphine, scopolamine and mefenamic acid; anti-epileptic therapeutic compounds, such as phenytoin sodium and sodium valproate; neuromuscular therapeutic compounds, such as dantrolene sodium; therapeutic compounds used in the treatment of diabetes, such as metformin, tolbutamide, diabenase glucagon and insulin; therapeutic compounds used in the treatment of thyroid gland dysfunction, such as triiodothyronine, thyroxine and propylthiouracil; diuretic therapeutic compounds, such as furosemide, chlortalidone, hydrochlorthiazide, spironolactone and triamterene; uterine relaxant therapeutic compounds, such as ritodrine; appetite suppressants, such as fenfluramine hydrochloride, phentermine and diethylproprion hydrochloride; anti-asthmatic therapeutic compounds, such as aminophylline, theophylline, salbutamol, orciprenaline sulphate and terbutaline sulphate, expectorant therapeutic compounds, such as guaiphenesin; cough suppressants, such as dextromethorphan and noscapine; mucolytic therapeutic compounds, such as carbocisteine; anti-septics, such as cetylpyridinium chloride, tyrothricin and chlorhexidine; decongestant therapeutic compounds, such as phenylpropanolamine and pseudoephedrine; hypnotic therapeutic compounds, such as dichloralphenazone and nitrazepam; anti-nauseant therapeutic compounds, such as promethazine theoclate; haemopoetic therapeutic compounds, such as ferrous sulphate, folic acid and calcium gluconate, uricosuric therapeutic compounds, such as sulphinpyrazone, allopurinoi and probenecid and the like.

The dry granulation process can be particularly suitable for certain types of active ingredients. In particular, the dry granulation process may provide advantages when applied to active ingredients that are poorly compressible, sensitive to dehydration or hydrolysis under typical granulation conditions, active ingredients for which it is desired to provide a relatively high ratio of active ingredient to carrier, such as for high dose pharmaceutical actives, as well as active ingredients sensitive to heating or high temperatures that may be encountered, for example, in melt granulation processes. The dry granulation process may also be used to produce extended or delayed release formulations.

The dry granulation process of the present disclosure can also be particularly suitable for active pharmaceutical ingredients that are sensitive to dehydration under heat or otherwise sensitive to heat in general. For these active pharmaceutical ingredients, excessive heat will decompose the active pharmaceutical ingredients, such as dehydration. As used herein, the term "sensitive to heat" means an active pharmaceutical compound which undergoes a minimum of 5% degradation at about 40° C. As used herein, the term "sensitive to dehydration" means an active pharmaceutical compound which undergoes a minimum of 5% dehydration at about 40° C.

The carrier used in the dry granulation process of the present disclosure is typically a polymeric material that has a melting point or a glass transition temperature not exceeding the melting point or melting range of the active ingredient. Examples of polymers suitable for use as carriers in the dry granulation process of the disclosure include, but are not limited to, homopolymers and copolymers of N-vinyl lactams, e.g., homopolymers and copolymers of N-vinyl pyrrolidone (e.g., polyvinylpyrrolidone), copolymers of N-vinyl pyrrolidone and vinyl acetate or vinyl propionate; cellulose esters and cellulose ethers (e.g., methylcellulose and ethylcellulose) hydroxyalkylcelluloses (e.g., hydroxypropylcellulose), hydroxyalkylalkylcelluloses (e.g., hydroxypropylmethylcellulose), cellulose phthalates (e.g., cellulose acetate phthalate and hydroxylpropylmethylcellulose phthalate) and cellulose succinates (e.g., hydroxypropylmethylcellulose succinate or hydroxypropylmethylcellulose acetate succinate); high molecular polyalkylene oxides such as polyethylene oxide and polypropylene oxide and copolymers of ethylene oxide and propylene oxide; polyacrylates and polymethacrylates (e.g., methacrylic acid/ethyl acrylate copolymers, methacrylic acid/methyl methacrylate copolymers, butyl methacrylate/2-dimethylaminoethyl methacrylate copolymers, poly(hydroxyalkyl acrylates), poly(hydroxyalkyl methacrylates)); polyacrylamides; vinyl acetate polymers such as copolymers of vinyl acetate and crotonic acid, partially hydrolyzed polyvinyl acetate; polyvinyl alcohol;

and oligo- and polysaccharides such as carrageenans, galactomannans and xanthan gum, or mixtures of one or more thereof.

Examples of derivatives of hydroxylpropylcellulose or ethylcellulose that are useful carriers for the present disclosure include anionic modifications, such as addition of a carboxymethyl moiety, cationic modifications, such as the provision of hydroxypropyltrimethylammonium salts, and nonionic modifications, such as addition of one or more alkyl or arylakyl moieties having 2 to 30 carbon atoms.

Examples of polysaccharides useful as carriers in the dry granulation process of the present disclosure include carboxymethylcellulose, hydroxyethylcellulose, methylcellulose, ethylhydroxyethylcellulose, hydroxyethylmethylcellulose, hydrophobically modified hydroxyethylcellulose, hydrophobically modified ethylhydroxyethylcellulose, carboxymethylhydroxyethylcellulose, carboxymethyl hydrophobically modified hydroxyethylcellulose, guar and guar derivatives, pectin, carrageenan, xanthan gum, locust bean gum, agar, algin and its derivatives, gellan gum, gum acacia, starch and modified starches. Examples of synthetic polymers useful as carriers in the dry granulation process of the present disclosure are mono- and co-polymers of carboxyvinyl monomers, mono- and co-polymers of acrylates or methacrylates monomers, mono- and co-polymers of oxyethylene, or oxypropylene monomers.

In some embodiments, the powder mixture includes a mixture of two or more carriers, one or more of which may be, for example, polymeric carriers. Each of the two or more carriers may be selected from the list provided above.

Suitable molecular weights for polymeric carriers used in this disclosure can be determined by a person of ordinary skill in the art, taking into consideration factors such as the desired polymer degradation rate, physical properties of the polymer such as mechanical strength and end group chemistry. Typically, a suitable range of molecular weight for the polymeric carrier is of from about 2,000 Daltons to about 2,000,000 Daltons, or from about 4,000 Daltons to about 1,800,000 Daltons, or from about 8,000 Daltons to about 1,600,000 Daltons, or from about 10,000 Daltons to about 1,400,000 Daltons, or from about 15,000 Daltons to about 1,200,000 Daltons, or from about 20,000 Daltons to about 1,000,000 Daltons, or from about 40,000 Daltons to about 1,000,000 Daltons.

In some embodiments, the active ingredient and carrier are mixed in a ratio in the range of about 99:1 to about 1:1 (on a dry weight basis) prior to, or upon addition into the feeder of the twin-screw extruder. In one exemplary embodiment, this ratio may be in the range of about 97:3 to about 60:40 (on a dry weight basis). In another embodiment, the ratio can be in a range of about 97:3 to about 75:25 (on a dry weight basis).

The dry granulation process of the present disclosure is also suitable for producing extended or delayed release formulations by selecting a suitable carrier. Polymeric carriers suitable for producing the extended release formulation include poly(lactides), poly(glycolides), poly(lactide-coglycolides), poly(lactic acid)s, poly(glycolic acid)s, polycarbonates, polyesteramides, polyanydrides, poly(amino acids), polyorthoesters, poly(dioxanone)s, poly(alkylene alkylate)s, polyethylene glycol and polyorthoester, biodegradable polyurethane, blends thereof.

There are other components that may be added to the powder mixture before dry granulation. These optional components include but are not limited to plasticizers, binders, fillers, lubricants, glidants, sweeteners, flavorants, colorants, and disintegrants. These components are required to be in a solid form at the barrel temperature of the screw barrel.

As used herein, the term "plasticizer" refers to a material that may be incorporated into the powder mixture in order to decrease the glass transition temperature and the melt viscosity of a polymer by increasing the free volume between polymer chains. The plasticizer can be present in concentration from about 0% to about 15%, e.g., about 0.5% to about 5% by weight of the powder mixture. Examples of plasticizers can be found in, for example, The Handbook of Pharmaceutical Excipients, 7th edition, Rowe et al., Eds., American Pharmaceuticals Association (2012); and Remington: the Science and Practice of Pharmacy, 22nd edition, Gennaro, Ed., Lippincott Williams & Wilkins (2012), which is hereby incorporated by reference in its entirety.

Examples of disintegrants include, but are not limited to, starches, clays, celluloses, alginates, gums, cross-linked polymers, e.g., cross-linked polyvinyl pyrrolidone or crospovidone, cross-linked sodium carboxymethylcellulose or croscarmellose sodium, and cross-linked calcium carboxymethylcellulose, soy polysaccharides, and guar gum. The disintegrant may be present in an amount of from about 0% to about 10% by weight of the powder mixture. In one embodiment, the disintegrant is present in an amount from about 0.1% to about 1.5% by weight of the powder mixture.

Examples of binders include, but are not limited to, starches, celluloses and derivatives thereof, for example, microcrystalline cellulose, hydroxypropyl cellulose hydroxylethyl cellulose and hydroxypropylmethyl cellulose, sucrose, dextrose, and polysaccharides. The binder may be present in an amount from about 0% to about 50%, e.g., about 10 to about 40% by weight of the powder mixture.

Examples of fillers and diluents include, but are not limited to, confectioner's sugar, compressible sugar, dextrates, dextrin, dextrose, lactose, mannitol, microcrystalline cellulose, powdered cellulose, sorbitol, sucrose and talc. The filler and/or diluent may be present in an amount of from about 0% to about 40% by weight, preferably about 15% to about 40% by weight of the powder mixture.

In some embodiments, the powder mixture may additionally contain a pH adjusting agent such as an acid or base mixed with the other powders prior to granulation. Suitable organic acids include citric acid, malic acid, maleic acid adipic acid, fumaric acid and the like. Suitable bases include calcium carbonate, sodium bicarbonate, calcium phosphate tribasic, dibasic sodium phosphate, sodium carbonate and the like.

The granules produced from such a powder mixture may be suitable for producing an extended release formulation.

In some embodiments, a powder lubricant may be added to the powder mixture for lubricating the screw barrel and rotating screws, thus preventing metal on metal contact during the dry granulation process. This powder lubricant can be selected to be a solid at the barrel temperature of screw barrel. Examples of powder lubricants include magnesium stearate, zinc stearate, lithium stearate, calcium stearate, aluminum stearate, sodium stearyl fumarate, talc, glyceryl behenate and colloidal silicon dioxide. Other suitable powder lubricants may include colloidal silica, magnesium trisilicate, starches, tribasic calcium phosphate, magnesium carbonate, magnesium oxide, polyethylene glycol, powdered cellulose and microcrystalline cellulose.

In one embodiment, the powder lubricant is added in an amount of from about 0.01 to about 1 wt. % of the powder mixture, or from about 0.05 to about 0.75 wt. % of the powder mixture, or from about 0.1 to about 0.5 wt. % of the powder mixture, or from about 0.15 to about 0.3 wt. % of the powder mixture, or from about 0.15 to about 0.25 wt. % of the powder mixture. In some embodiments, the powder lubricant is preferably added to the powder mixture during the final stage of geometric dilution of the powder mixture because it was found that, in some embodiments, earlier addition of the lubricant may prevent forming of granules with desired hardness.

As used herein, the term "geometric dilution" is a pharmaceutical term referring to the extemporaneous method of efficiently combining two unequal amounts of a powdered substance to form a homogenous mixture. The concept of geometric dilution centers on the successive addition and blending of equal quantities of materials.

In some embodiments where little or no powder lubricant is added to the powder mixture, the rotation speed for the screws of the twin-screw extruder may be less than about 200 rpm, or less about 180 rpm, or less than about 160 rpm, or less than about 140 rpm, or less than about 130 rpm, or less than about 120 rpm, or less than about 110 rpm, or less than about 100 rpm, or less than about 90 rpm, or less than about 80 rpm, or less than about 70 rpm, or less than about 60 rpm. In some embodiments, the rotation speed for the screws of the twin-screw extruder can be between about 10-200 rpm, about 25-150 rpm, about 25-100 rpm, or about 25-50 rpm.

In some embodiments, the feed rate into the twin-screw extruder is less than about 500 g/hr, less than about 400 g/hr, less than about 300 g/hr, less than about 250 g/hr, less than about 200 g/hr, less than about 150 g/hr, less than about 100 g/hr, or less than about 50 g/hr. In some embodiments, the feed rate into the twin-screw extruder is about 10-500 g/hr, about 25-300 g/hr, about 38-300 g/hr, about 80-300 g/hr, about 80-240 g/hr, about 80-180 g/hr, or about 100-180 g/hr. In some embodiments, the feed rate can be higher than 500 g/hr.

The twin-screw extruder typically extrudes granules that are in fiber-like shape. The fiber-like granules are often chopped or milled into particles that may later be filled into capsules or sachets, or compressed into tablets. In some embodiments, the twin-screw extruder may additionally comprise a chopping device for chopping the fiber-like granules into particles. The chopping device can be preferably placed proximate to the die block such that the granules discharged from the die block are immediately chopped into particles.

In some other embodiments, the granules may be collected from the twin-screw extruder and cooled. The cooled granules can be milled to produce particles of desired sizes. Once the cooled granules or milled particles are obtained, they may be formulated into formulations, such as tablets, pills, lozenges, caplets, capsules or sachets. These formulations may include additional conventional carriers as an external phase of the pharmaceutical composition. These carriers are located on the outside of the granules and thus are referred to as extragranular carriers, to be distinguished from the intragranular carrier(s) that are present during the dry granulation process.

Examples of such extragranular carriers include, but are not limited to, release retardants, plasticizers, disintegrants, fillers, binders, lubricants, glidants, stabilizers, fillers and diluents. The plasticizers, non-polymeric carriers, binders, fillers and disintegrants have been discussed above. The amount of each extragranular carrier used may vary within ranges conventional in the art. The following references which are all hereby incorporated by reference herein disclose techniques and carriers used to formulate oral dosage formulations. See The Handbook of Pharmaceutical Excipients, 7th edition, Rowe et al., Eds., American Pharmaceuticals Association (2012); and Remington: the Science and Practice of Pharmacy, 22nd edition, Gennaro, Ed., Lippincott Williams & Wilkins (2012).

Once the granules are compressed into tablets, they can be optionally coated with a functional or nonfunctional coating as known in the art. Examples of coating techniques include, but are not limited to, sugar coating, film coating, microencapsulation and compression coating. Types of coatings include, but are not limited to, extended or delayed release coatings.

The disclosure also comprises granules produced by the dry granulation process of the disclosure, as well as tablets and capsules made from such granules including oral dosage forms containing an active pharmaceutical ingredient and high dosage oral formulations containing an active pharmaceutical ingredient.

In some embodiments, the time to 80% dissolution of the tablet or other solid formulation produced from the granules disclosed herein is about 1-20 hours, about 3-20 hours, about 5-15 hours, or about 12-14 hours. In some embodiments, the time to 100% dissolution or 100% drug release is about 1-20 hours, about 5-20 hours, about 6-18 hours, about 10-18 hours, or about 12-16 hours.

It must be noted that as used herein and in the appended claims, the singular forms "a", "an", and "the" include plural references unless the context clearly dictates otherwise. Furthermore, the terms "a" (or "an"), "one or more", and "at least one" can be used interchangeably herein. The terms "comprising", "including", "having" and "constructed from" can also be used interchangeably.

Unless otherwise indicated, all numbers expressing quantities of ingredients, properties such as molecular weight, percent, ratio, reaction conditions, and so forth used in the specification and claims are to be understood as being modified in all instances by the term "about," whether or not the term "about" is present. Accordingly, unless indicated to the contrary, the numerical parameters set forth in the specification and claims are approximations that may vary depending upon the desired properties sought to be obtained by the present disclosure and the normal expected variation in the art. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

It is to be understood that each component, compound, substituent, or parameter disclosed herein is to be interpreted as being disclosed for use alone or in combination with one or more of each and every other component, compound, substituent, or parameter disclosed herein.

It is also to be understood that each amount/value or range of amounts/values for each component, compound, substituent, or parameter disclosed herein is to be interpreted as also being disclosed in combination with each amount/value or range of amounts/values disclosed for any other component (s), compounds(s), substituent(s), or parameter(s) disclosed herein and that any combination of amounts/values or ranges of amounts/values for two or more component(s), compounds(s), substituent(s), or parameters disclosed herein are thus also disclosed in combination with each other for the purposes of this description.

It is further understood that each lower limit of each range disclosed herein is to be interpreted as disclosed in combination with each upper limit of each range disclosed herein for the same component, compounds, substituent, or parameter. Thus, a disclosure of two ranges is to be interpreted as a disclosure of four ranges derived by combining each lower limit of each range with each upper limit of each range. A disclosure of three ranges is to be interpreted as a disclosure of nine ranges derived by combining each lower limit of each range with each upper limit of each range, etc. Furthermore, specific amounts/values of a component, compound, substituent, or parameter disclosed in the description or an example is to be interpreted as a disclosure of either a lower or an upper limit of a range and thus can be combined with any other lower or upper limit of a range or specific amount/value for the same component, compound, substituent, or parameter disclosed elsewhere in the application to form a range for that component, compound, substituent, or parameter.

The following examples are illustrative, but not limiting, of the soft gelatin capsules of the present disclosure. Other suitable modifications and adaptations of the variety of conditions and parameters normally encountered in the field, and which are obvious to those skilled in the art, are within the scope of the disclosure.

EXAMPLES

Example 1: Dry Granulation of Sildenafil Citrate

Sildenafil citrate was formulated into a high drug dose, extended release tablet formulation using the twin-screw dry granulation process of the present disclosure. Specifically, the granules' surface morphology, sildenafil citrate crystalline structure, high drug dose, sildenafil citrate phase changes, chemical interactions, and conventional granule properties including compressibility index, angle of repose, and Hausner ratio, were used as quality requirements.

The methods used in this example for assessing the product quality included evaluating drug uniformity in tablets in accordance with United States Pharmacopeia (USP) specification ranges, assessment of conventional granule and uncoated tablet properties (as outlined in the USP), differential scanning calorimetry (DSC), thermogravimetric analysis (TGA), hot stage microscopy (HSM), mid-infrared (MIR) spectroscopy, and scanning electron microscopy (SEM).

The materials used in this example included hydroxyethyl cellulose (HEC, Natrasol™ 250 L), ethyl cellulose (EC, Aqualon™ N7), hydroxypropyl cellulose (HPC, Klucel™ HF) and sildenafil citrate, obtained from Ashland Specialty Ingredients (Wilmington, Del.). Magnesium stearate, hydrochloric acid and the solvents used in this example (analytical grade methanol) were purchased from Fisher Scientific (Norcross, Ga.).

Prior to drug granulation, the polymers (hydroxyethyl cellulose, ethyl cellulose, hydroxypropyl cellulose) were sieved using a USP #35 mesh screen to remove any aggregates that may have formed. The components (sildenafil citrate and polymers) used in each powder mixture were geometrically diluted using a glass mortar and pestle.

Various screw designs with different configurations were used in this example, as shown in FIGS. 2A-2E. FIG. 2A shows a screw design that was similar to those used in polymer processing or hot-melt extrusion operations, which had numerous mixing elements capable of imparting considerable shear to the powder mixture. This configuration consistently resulted in melting the powder mixture at any appreciable screw speed. The screw design shown in FIG. 2B consisted of all conveying elements but no mixing elements. This configuration merely pumped the powder mixture through the extruder's screw barrel without granulation of the powder mixture.

The screw design shown in FIG. 2C had three mixing elements added near the discharge end of the screw design shown in FIG. 2B. The screw design of FIG. 2C was capable of producing granules. Two additional screw designs shown in FIGS. 2D-2E were shown to be capable of producing granules. In FIG. 2D, the screw design had an additional mixing element, relative to the design of FIG. 2C, added closer to the feeding zone. The screw design in FIG. 2E was a modified version of the screw design in FIG. 2D where the mixing elements near the discharge section of the screw were altered to change the offset angle.

Figure 3A:
FIGS. 3A-3B are photos showing differences between a molten powder mass on the mixing elements of twin screws (FIG. 3A) and a compacted powder mass formed during the twin-screw dry granulation process of the disclosure (FIG. 3B).
Figure 3B:
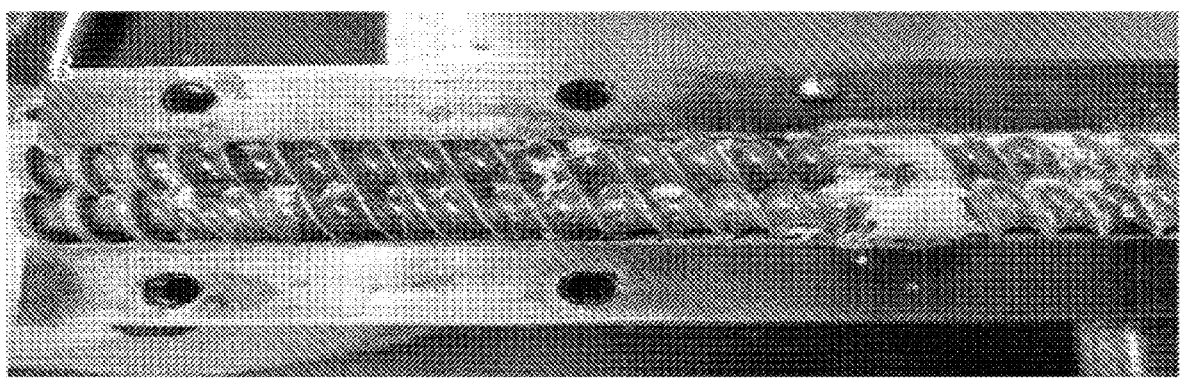

FIGS. 3A-3B provide a visual comparison of the powder mixture in the mixing zones of a screw barrel used in hot melt extrusion process and a dry granulation process, respectively. The dry powder mixture of FIG. 3B was being conveyed and kneaded in the mixing zone of the screw barrel in a dry granulation process. The matte appearance of the powder mixture in the mixing zone indicates that the mass on the mixing elements was in a dry compacted form. Additionally, the ability to easily crush the compacted mass back into a fine powder further indicated that dry agglomerates were being formed. In contrast, the material in the mixing zone in a hot melt extrusion as shown in FIG. 3A had a glossy appearance that commonly results from complete melting of polymers. The melted mass could not be easily removed, nor crushed back into its original fine powder form.

In order to prevent product degradation and/or contamination as well as damage to the twin-screw extruder, a solid lubricant (magnesium stearate) was added to the powder mixture of sildenafil citrate and polymeric intragranular carrier. The same lubricant was also used as an extragranular carrier to reduce noise during a later tableting process step.

While the addition of modest amounts of magnesium stearate (0.2%) eliminated the grinding noises from the extruder, it was observed that relatively larger quantities (0.5%) resulted in unacceptably high portion of fine powders exiting the screw barrel. The addition of even larger quantities of magnesium stearate (1.0%) frequently prevented the formation of granules entirely. The addition of magnesium stearate into the powder mixture needed to occur during the final stage of geometric dilution of the drug as earlier addition would also prevent granule formation. Finally, when the quantity of lubricant was not sufficient to eliminate the noise from the extruder, the screw speed was limited to a maximum of 200 rpm. The percent of intergranular magnesium stearate added to the powder mixture for lubricating the screws was fixed at 0.2%, while extragranular magnesium stearate used to lubricate the tablet machine was fixed at 0.5%.

A buildup of back pressure was required to facilitate the agglomeration of some compositions.

All of the tested polymers (ethyl cellulose (EC), hydroxypropyl cellulose (HPC) & hydroxyethyl cellulose (HEC)) were found capable of producing granules using the dry granulation process of the present disclosure, though this example used polymeric carriers that were blends of HPC and HEC.

A fully intermeshing, co-rotating, twin-screw extruder (11 mm Process 11™, ThermoFisher Scientific) was used to dry granulate a powder mixture of sildenafil citrate and polymers (HPC and HEC blends). After allowing the extruder to reach steady state, the produced granules were collected from the extruder and stored in polyethylene bags for further processing and/or analysis.

Steady state processing was observed to have occurred when each zone of the extruder barrel, excluding the hopper, maintained a temperature of 65° C. (constant for all experiments), and the feed rate of 3-5 g/min. and screw speed (100, 150 or 200 rpm) were maintained for a duration exceeding the residence time of the in-process material.

The granules were used to produce tablets using a single station tablet press (Globe) with an 8.0 mm flat face tooling. The compression force was set to 100, 200, or 300 kg/cm2. Compression forces greater than 300 kg/cm2 resulted in formulation leakage around the compression tooling. The addition of 0.2% magnesium stearate as an extragranular carrier prevented adherence of granulated particles or the complete dosage form to the tooling (picking and sticking).

A dual scooping projection Vanderkamp friabilator (Vankel Industries Inc. Chatham, N.J.) was used to assess tablet friability. The friabilator was filled with 33 tablets (at 200 mg each) in one side and allowed to rotate continuously for four minutes at 25 rpm. The tablets were accurately weighed prior to the test, and carefully de-dusted and reweighed after the test. The weight reduction was indicative of the tablet friability.

Tablet hardness was assessed using a Schleuniger hardness tester. Each tablet was placed firmly against the stationary anvil prior to beginning the test, and all debris from the previous test was carefully removed before performing replicate tests (n=10). Weight variations in the tablets were measured on a microbalance. Twenty tablets were weighed, and their average determined. The weight of the individual tablets was then compared to the average and evaluated within USP specified tolerances for uncoated tablets (±7.5%).

The tablets were assessed for in vitro drug release in 900 ml gastric media (0.01N HCl) using USP apparatus I (Hanson SR8) at 37±0.5° C. with a basket rotation speed of 100 rpm over a 24 hour period. The dissolution vessels were equipped with UV-Vis fiber optic probes (Rainbow Dissolution Monitor, pION) and the detector was set at a wavelength of 290 nm.

The hardness and friability of the tablets in 16 runs are presented in Table 2.

TABLE 2

Tablet Friability and Hardness

| Run | Friability (%) | Hardness (kp) |
|---|---|---|
| 1 | 0.04970179 | 15.76667 |
| 2 | 0.18181818 | 15.96667 |
| 3 | 0.09955202 | 15.86667 |
| 4 | 0.09861933 | 18.73333 |
| 5 | 0 | 11.53333 |
| 6 | 0.04945598 | 12.6 |
| 7 | 0.15052684 | 14.03333 |
| 8 | 0.29865605 | 8.566667 |
| 9 | 0.0990099 | 13.63333 |
| 10 | 0.05005005 | 11.2 |
| 11 | 0 | 12.1 |
| 12 | 0 | 11.76667 |
| 13 | 0 | 15.03333 |
| 14 | 0.05037783 | 17.3 |
| 15 | 0.04985045 | 13.4 |
| 16 | 0.15052684 | 14.4 |

The fractional factorial model with two center points was utilized to determine which granulation parameters caused the most significant effects. The final product quality and the ranges of the parameters, as well as the main factors that provided a statistically significant contribution to the responses are listed in Table 3.

TABLE 3

Statistically Significant Main Factors

| Response | Range | Main Effect(s) |
|---|---|---|
| Percent Fines | 12-49% | Screw Configuration, Polymer Ratio & Drug Loading |
| Angle of Repose | 22.02-38.66 | Polymer Ratio |
| Compressibility Index | 4.76-28.17 | Screw Configuration |
| Hausner Ratio | 1.05-1.39 | Screw Configuration |
| API Crystallinity | Always Maintained | N/A |
| Tablet Hardness | 8.6-18.7 | Screw Configuration, Compression Force & Drug Loading |
| Tablet Friability | 0-0.3 | Drug Loading & Screw Speed |
| Time to 80% Dissolution | 3-15.5 | Polymer Ratio & Drug Loading |

After the fractional factorial model, a full factorial ($2^3$) model with four center points (Table 4) was used to evaluate interactions between the main factors, and to numerically determine best values for the main factors (granulation parameters). The extruder's volumetric feeder output was set to 4 g/min and the screw speed was maintained at 150 rpm. The barrel temperature was held at 65° C. from zone 2 to the barrel exit (granule discharge, see also Table 1). The statistically significant main factors (granulation parameters) and their interactions are listed in Table 5.

TABLE 4

$2^3$ Full Factorial with 4 Center Points

| Run | Screw Design | Polymer Ratio (HPC:HEC) | Drug Loading (%) | Fines (%) | Hausner Index | Compress-ibility | 80% Disso. (hr.) |
|---|---|---|---|---|---|---|---|
| 1 | 1 | 3:1 | 50 | 13.2 | 1.32 | 24 | 12.5 |
| 2 | 2 | 1.7:1 | 42.5 | 14.0 | 1.34 | 25 | 11.5 |
| 3 | 2 | 3:1 | 35 | 10.5 | 1.29 | 22 | 15 |
| 4 | 2 | 1:1 | 35 | 13.5 | 1.16 | 14 | 11.5 |
| 5 | 1 | 1.7:1 | 42.5 | 13.1 | 1.26 | 21 | 14 |
| 6 | 1 | 1.7:1 | 42.5 | 10.3 | 1.32 | 24 | 12 |
| 7 | 1 | 1:1 | 50 | 17.1 | 1.30 | 23 | 8.5 |
| 8 | 2 | 1.7:1 | 42.5 | 13.2 | 1.32 | 24 | 12 |
| 9 | 2 | 1:1 | 50 | 10.7 | 1.25 | 20 | 6.5 |
| 10 | 1 | 3:1 | 35 | 10.7 | 1.19 | 16 | 15 |
| 11 | 2 | 3:1 | 50 | 12.6 | 1.24 | 19 | 11 |
| 12 | 1 | 1:1 | 35 | 11.0 | 1.29 | 23 | 8 |

TABLE 5

Response Ranges and Statistically Significant Main Factors

| Response | Range | Main Factors and Interactions |
|---|---|---|
| Percent Fines | 10.32-17.08% | Screw Configuration, Polymer Ratio & Drug Loading (3 way interaction) |
| Compressibility Index | 13.51-25.37 | Screw Configuration, Polymer Ratio & Drug Loading (3 way interaction) |
| Hausner Ratio | 1.16-1.34 | Screw Configuration, Polymer Ratio & Drug Loading (3 way interaction) |
| Time to 80% Dissolution | 6.5-15 | Polymer Ratio & Drug Loading (Main Effects) |

The potentially suitable dry granulation settings are given in Table 6.

The screw design 1 in Table 6 was the screw configuration of FIG. 2D and the screw design 2 in Table 6 was the screw configuration of FIG. 2E. Setting number 1 was selected as it incorporated the highest drug loading and it possessed the highest desirability. The predicted values of setting number 1 and predicted product properties were then compared to the measured values (Table 7).

TABLE 6

Predicted Dry Granulation Settings

| Number | Screw Configuration | Polymer Ratio | Drug Load | Hausner Index | Compressibility | Time to 80% Dissolution | Desirability |
|---|---|---|---|---|---|---|---|
| 1 | 1 | 0.75 | 42.69 | 1.25 | 19.7 | 13.82 | 0.558 |
| 2 | 1 | 0.75 | 41.56 | 1.24 | 19.36 | 13.9 | 0.526 |
| 3 | 2 | 0.61 | 36.90 | 1.25 | 20.98 | 12.9 | 0.196 |
| 4 | 2 | 0.61 | 36.68 | 1.25 | 21.03 | 13.0 | 0.194 |

TABLE 7

Measured Values of #1 Setting No. 1

| Number | Screw Configuration | Polymer Ratio | Drug Load | Hausner Index | Compressibility | Time to 80% Dissolution | Desirability |
|---|---|---|---|---|---|---|---|
| 1 | 1 | 0.75 | 42.69 | 1.22 | 21.1 | 14 | 0.558 |

The selected setting number 1 was used as the dry granulation process and its products were further evaluated. The crystalline structure of sildenafil citrate in the tablets was studied using Fourier Transform Infrared Spectroscopy (FT-IR). Mid-infrared spectral analysis was conducted on an FT-IR bench (Agilent Technologies Cary 660, Santa Clara, Calif.). The FT-IR bench was equipped with an ATR (Pike Technologies MIRacle ATR, Madison, Wis.), which was fitted with a single bounce diamond coated ZnSe internal reflection element. The spectra were collected over a range of 4000-650 cm-1. Spectral analysis was conducted using the Resolutions Pro software suite (Agilent Technologies, Calif.).

Figure 4:
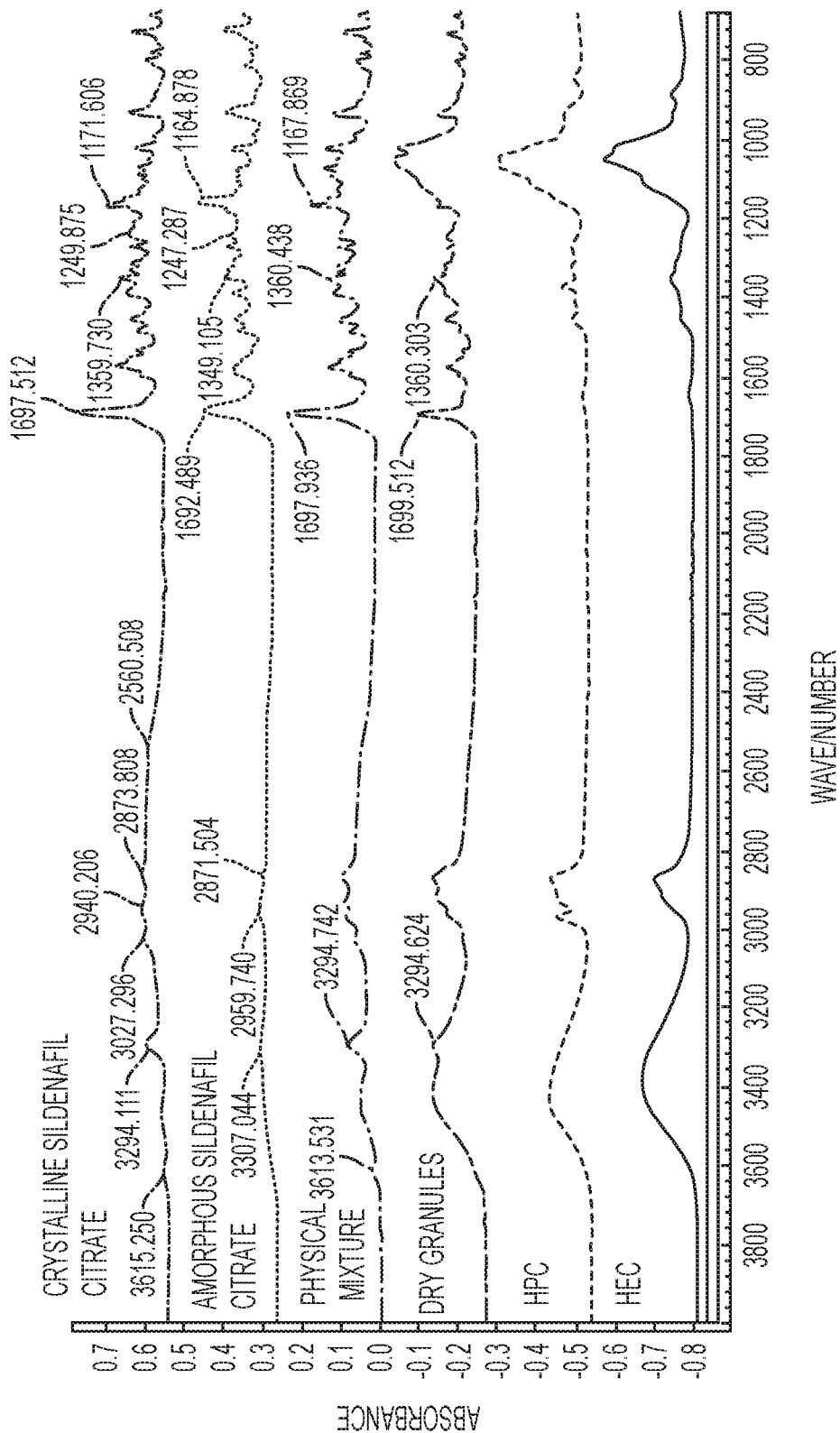
FIG. 4 illustrates a mid-infrared spectrum of the granules produced in Example 1.

FT-IR spectral analysis (FIG. 4) showed that the amorphous phase of sildenafil citrate exhibited shifted, shorter and broader spectral bands relative to the crystalline phase. This allowed confirmation that the sildenafil citrate's crystalline structure was preserved in the tablets.

Scanning Electron Microscopy (SEM) was used to assess the surface morphology of three samples: the powder mixture, melt extruded granules, and the dry granules extruded from the powder mixture. Prior to sample mounting, the surfaces of the samples were cut with a razor in order to provide a flat surface. These samples were sputter coated with gold under an argon atmosphere using a Hummer 6.2 Sputter Coater (Ladd Research Industries, Williston, Vt., US) under a high-vacuum evaporator equipped with an omni-rotary stage tray to help ensure uniform coating. The images were captured at multiple magnifications using a JSM-5600 scanning electron microscope (JEOL USA, Inc., Waterford, Va., US) at an accelerating voltage of 5 kV.

Example 2: Dry Granulation of Ondansetron

This example used ondansetron (OND) as an example of a heat-labile pharmaceutical compound in the dry granulation process. OND is a serotonin 5-HT3 receptor antagonist for treating and preventing nausea and vomiting induced by chemotherapy/radiotherapy/cancer surgery. OND exists in a dihydrate form and is susceptible to dehydration when exposed to heat. This example examined the dehydration behavior of OND during the twin-screw dry granulation process.

The materials used in this example were OND (i.e., Ondansetron HCl dihydrate) purchased from Chemscene LLC (New Jersey, USA), hydroxyl-propyl cellulose (Klucel™ EF) from Ashland Specialty Ingredients (Wilmington, Del.), ethyl cellulose (Ethocel Standard 10) from Dow chemical company. All other reagents were analytical grade.

20 wt. % OND, 79.5 wt. % polymers with ethyl cellulose (EC) and hydroxyl-propyl cellulose (HPC) in a ratio of 1:1 and 0.5 wt. % magnesium stearate were first individually passed through a US #35 mesh to remove aggregates. The sieved ingredients were then thoroughly mixed to prepare a powder mixture using a V-shell blender (GlobePharma, Maxiblend™ New Brunswick, N.J.) for 20 min at 25 rpm. The prepared powder mixture was fed into a co-rotating twin-screw extruder (11 mm Process 11™, Thermo-Fisher Scientific Karlsruhe, Germany) using a volumetric feeder.

Figure 5:
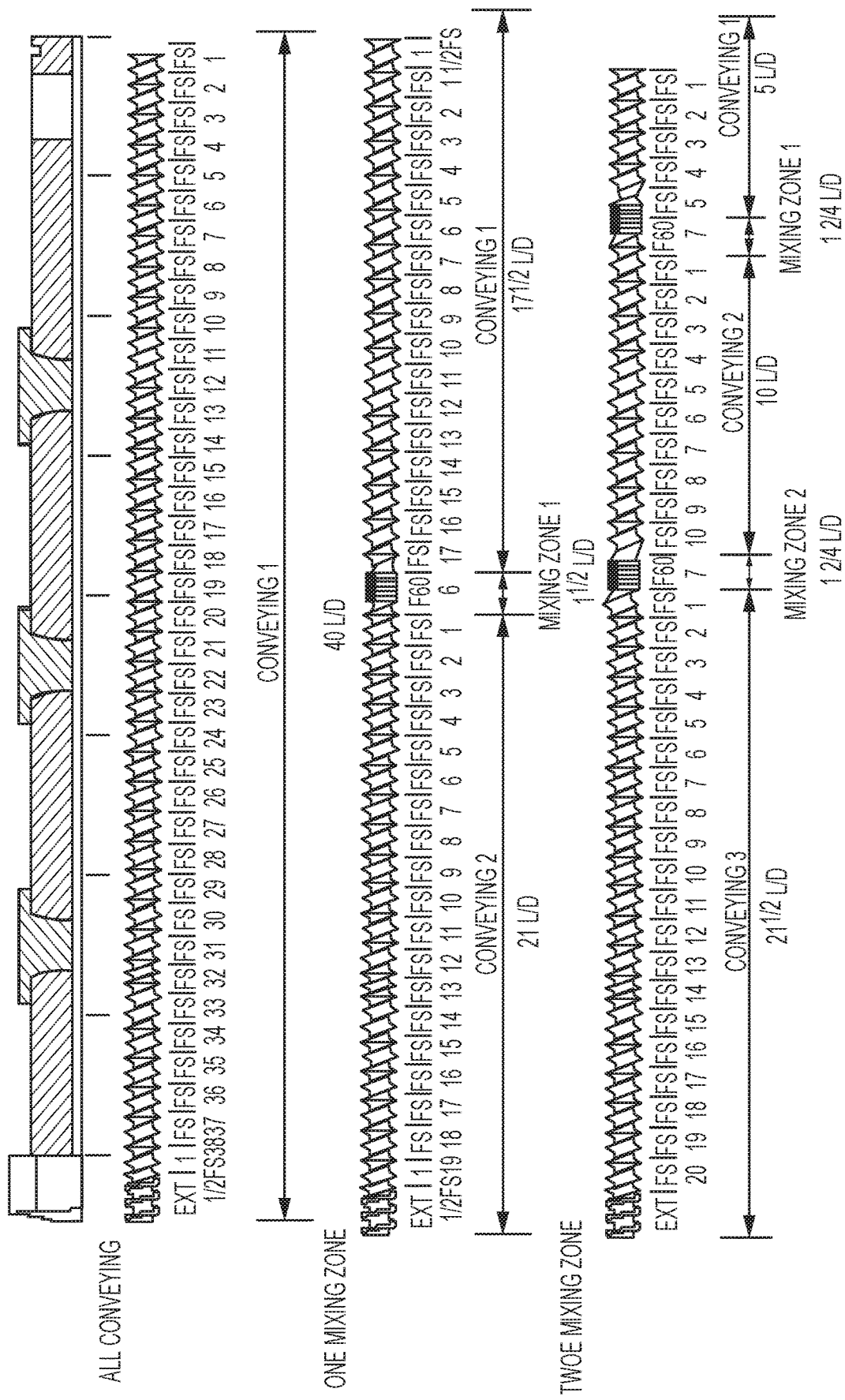
FIG. 5 illustrates various screw configurations that were used in the twin-screw extruder to carry out the dry granulation methods of Example 2.

Dry granulation was performed using the screw configuration, screw speed, and barrel temperatures shown in Tables 8 and 9. One screw configuration had no mixing zone (configuration 1), the second configuration containing one mixing element along with the conveying elements (configuration 2) and the third configuration containing two mixing elements along with the conveying elements (configuration 3) (FIG. 5). The produced dry granules were then characterized to evaluate the solid-state phase transformation of OND.

TABLE 8

Dry Granulation Parameters

| Screw Config. | Barrel temperatures (° C.) in zones of the screw barrel | | | | | | | | Screw speed (rpm) | Feed rate (g/hr) |
|---|---|---|---|---|---|---|---|---|---|---|
| | Feed | 2 | 3 | 4 | 5 | 6 | 7 | 8 | Die | | |
| 1 | N/A | 140 | 140 | 140 | 140 | 50 | 50 | 50 | 40 | 25 or 100 | 80 |
| 2 | N/A | 110 | 110 | 110 | 110 | 50 | 50 | 50 | 40 | 25 or 100 | 80 |
| 3 | N/A | 90 | 90 | 90 | 90 | 50 | 50 | 50 | 40 | 25 or 100 | 80 |

TABLE 9

Dry Granulation Batches and Parameters

| Batch # | Screw Configuration | Highest barrel temp (° C.) | Screw speed (rpm) |
|---|---|---|---|
| A1 | 3 | 90 | 100 |
| A2 | 3 | 90 | 25 |
| A3 | 3 | 110 | 100 |
| A4 | 3 | 110 | 25 |
| A5 | 3 | 140 | 100 |
| A6 | 3 | 140 | 25 |
| A7 | 1 | 90 | 25 |
| A8 | 1 | 90 | 100 |
| A9 | 1 | 110 | 25 |
| A10 | 1 | 110 | 100 |
| A11 | 1 | 140 | 25 |
| A12 | 1 | 140 | 100 |
| A13 | 2 | 90 | 25 |
| A14 | 2 | 90 | 100 |
| A15 | 2 | 110 | 25 |
| A16 | 2 | 110 | 100 |
| A17 | 2 | 140 | 25 |
| A18 | 2 | 140 | 100 |

Diamond differential scanning calorimetry (DSC, Perkin Elmer Life and Analytical Sciences, Waltham, Mass., USA) was used to study the phase transformation of OND as 3-5 mg of pure OND, as a powder mixture of OND/polymers, and as granules produced by dry granulation. These samples were weighed and hermetically sealed in aluminum pans. Thermal analyses of the samples were performed over a temperature range of 25-250° C. at a heating rate of 10° C./min under an inert nitrogen atmosphere at a flow rate of 20 mL/min. Endothermic onset and peak temperature of melting were calculated from the obtained thermogram using Pyris™ Manager software (PerkinElmer Life and Analytical Sciences, 719 Bridgeport Ave., Conn., USA).

Figure 6:
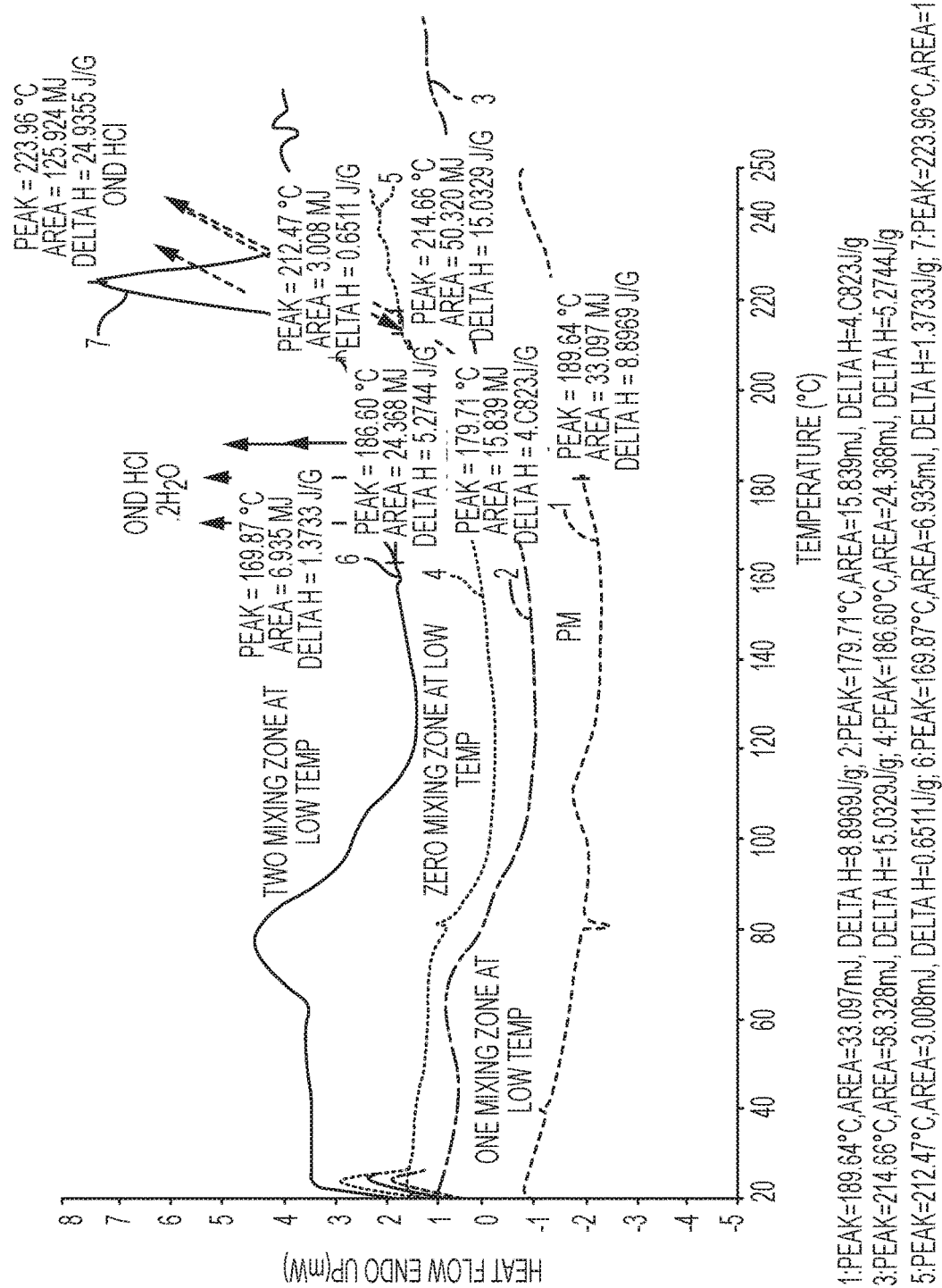
FIG. 6 is a differential scanning calorimetry (DSC) thermogram showing dehydration of ondansetron HC1.2H20 to ondansetron HC1, using the screw configurations of FIG. 5 in the methods of Example 2.

The effects of screw configuration on OND phase transformation are shown in FIG. 6. OND-polymer/powder granulated using screw configuration 1 exhibited the characteristic melting peak of OND at 189° C., which was the same as the powder mixture corresponding to the OND dihydrate form. Using screw configuration 2, the melting peak shifted from 189° C. to 179° C. and there was a new endothermic peak at 214° C. When screw configuration 3 was used the endothermic peak corresponding to the dihydrate form shifted to a lower temperature (at 169° C.) and a new endothermic peak of the dehydrated form was observed at 223° C. Therefore, the increased number of mixing elements on the screw resulted in more intense mixing and higher shear being exerted on the powder mixture in the screw barrel.

Figure 7:
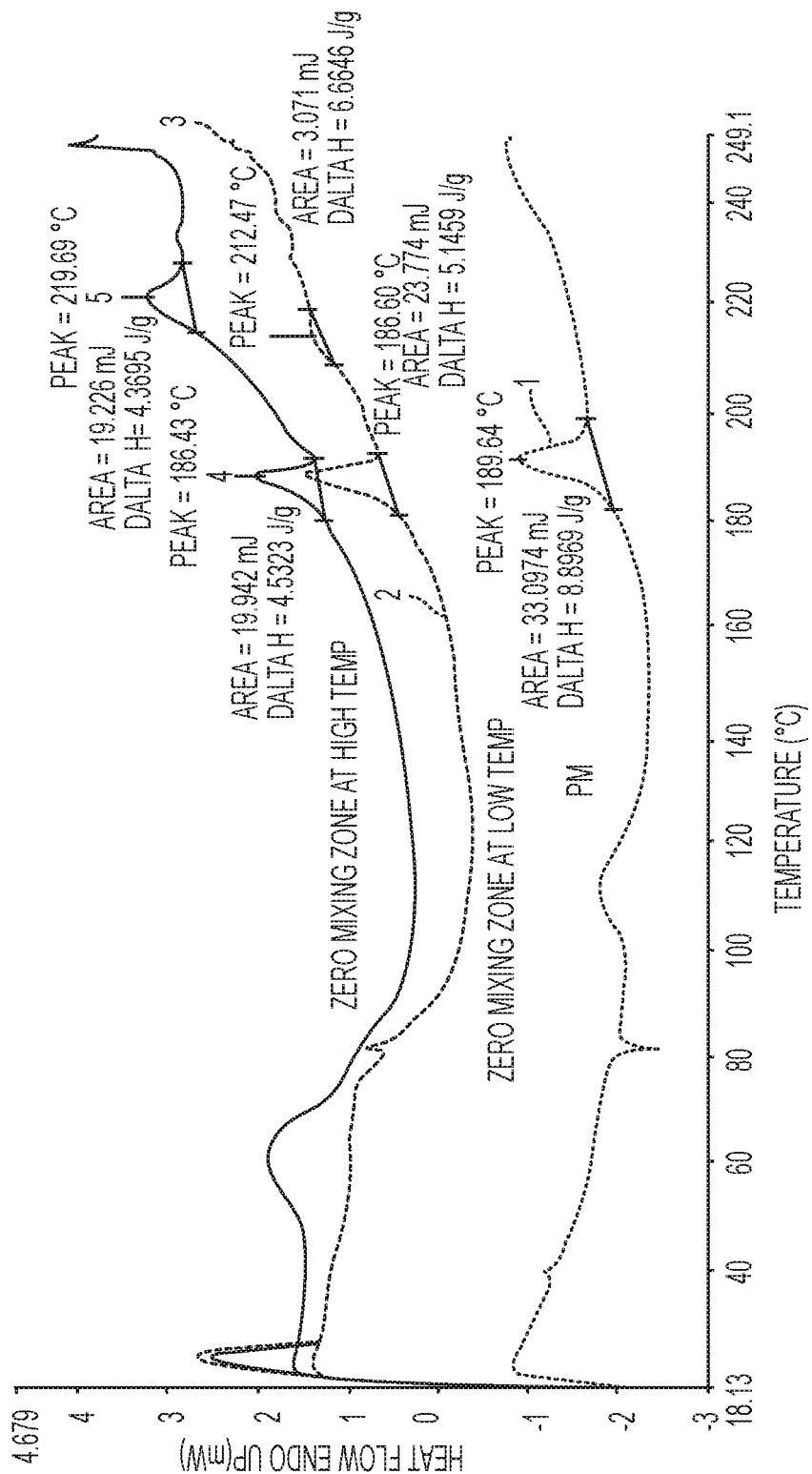
FIG. 7 is a DSC thermogram showing dehydration of ondansetron HC1.2H20 to ondansetron HC1 at various processing conditions.

In the dry granulation process, two factors were responsible for granulating the powder mixture: thermal energy from the heated barrel and applied shear mechanical energy. It was also observed that an increase in the number of mixing elements on the screws (and thus a corresponding increase in applied shearing energy) caused further dehydration of OND HCl-2H2O. The effects of screw barrel temperature on OND phase transformation are shown in FIG. 7. The DSC results showed that there was no shift in the melting peak of OND at low granulation barrel temperatures when screw configuration 1 was utilized, but at high barrel temperatures a new endothermic peak appeared at 219° C. corresponding to a peak of dehydrated OND. Using screw configuration 3 at a high barrel temperature, only one endothermic peak was observed at 217° C., which confirms that the OND had undergone complete dehydration.

Twin screw technology can be utilized for continuous high shear dry granulation. It can achieve the desired level of mixing by a combination of the appropriate screw configuration and a suitable set of process settings (e.g. feed rate, screw speed, etc.), thereby producing a certain granule size and shape distribution. In this process, plastic deformation of the powders can be induced to facilitate bonding into a compact for subsequent milling into granules. Powders can be confined within the particular screw configuration design and as such, subjected to a compressive stress can rearrange until there is insufficient free volume to allow translation of particles. As the stress increases, particles can make contacts which increase in areas with stress. They can deform elastically (i.e. reversibly) with Young's modulus as the linear proportionality constant. This process is also known as consolidation. Consolidation can be described as the increase in the mechanical strength of a material as a result of particle/particle interactions. When the surfaces of two particles approach each other closely enough (e.g. at a separation of less than 50 nm), their free surface energies can result in a strong attractive force through a process known as cold welding. This can be major reason why the mechanical strength of a bed of powder increases when subjected to rising compressive forces within the twin screw extruder.

Figure 8:
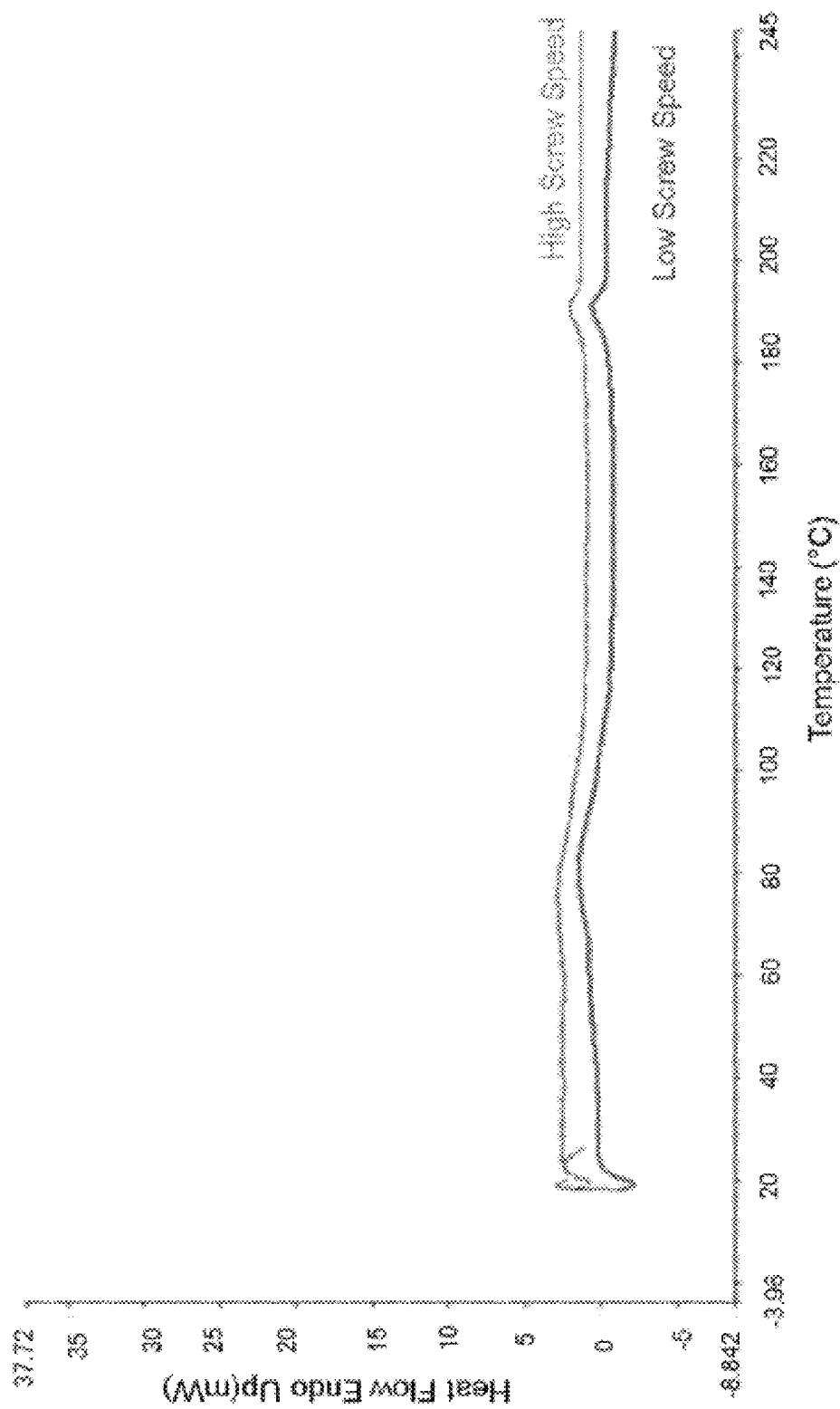
FIG. 8 is a DSC thermogram showing dehydration of ondansetron HC1.2H20 to ondansetron HC1, using a low barrel temperature and the conveying screw configuration 1 of FIG. 5 at various screw speeds.

The effects of screw speed on OND phase transformation are shown in FIG. 8. The granules were prepared using both high and low screw speeds at a low barrel temperature. For both screw speeds, the melting endothermic peak of OND was 190° C., indicating that screw speed did not significantly affect OND dehydration.

Figure 9:
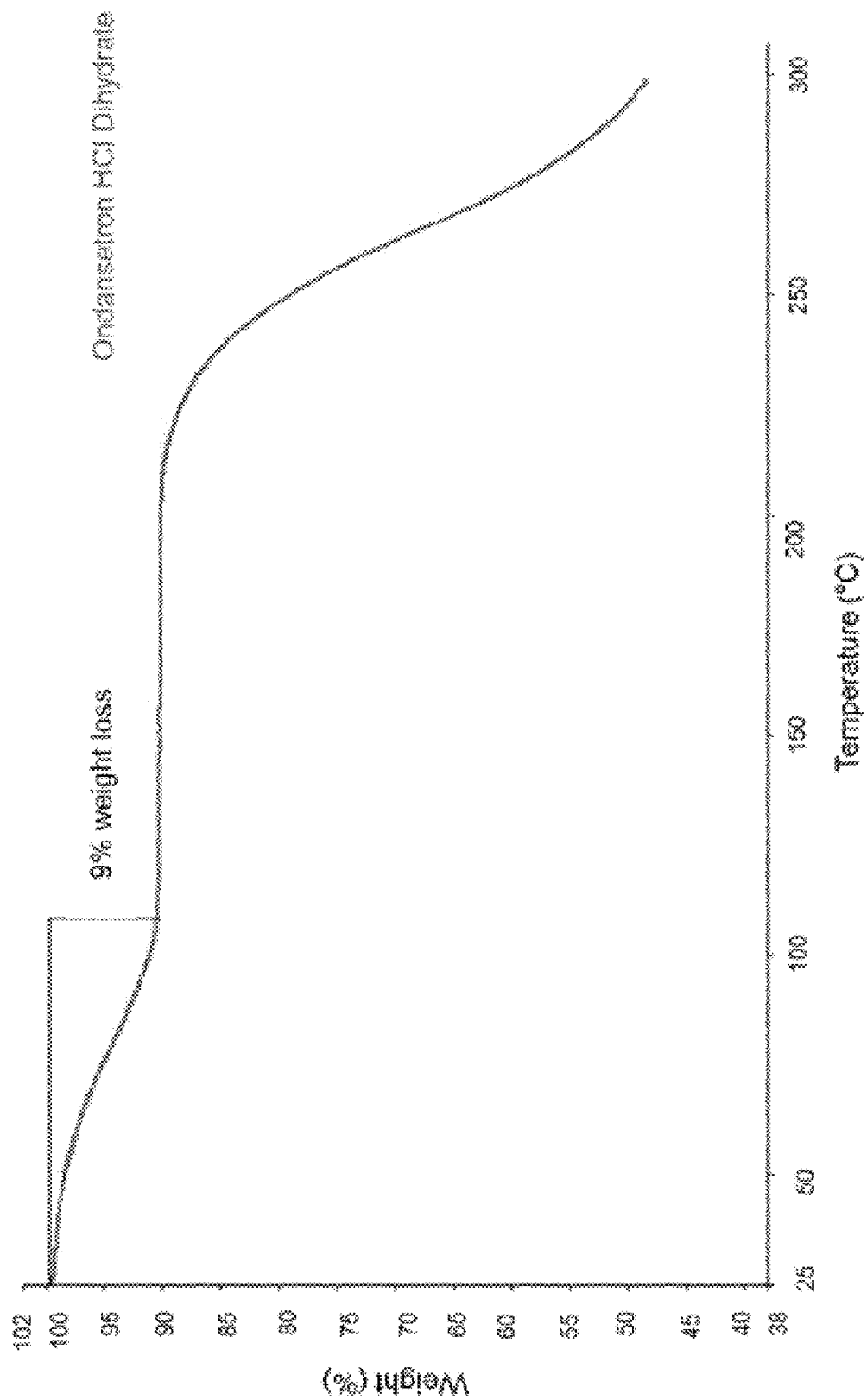
FIG. 9 is a plot showing a thermogravimetric analysis of the ondansetron HC1.2H20 of Example 2.

Thermogravimetric analysis (TGA) was used to determine weight loss of OND due to dehydration. A weighed sample of OND was heated from 25° C. to 300° C. at a rate of 20° C./min in a platinum pan under an inert nitrogen atmosphere purge flowing at a rate of 20 ml per minute. The TGA thermogram of OND is presented in FIG. 9. Heating caused loss of 2 moles of loosely bound water from each mole of OND dihydrate. As shown in FIG. 9, about 10% of the weight was lost when OND was heated from 60-105° C., which was in agreement with the theoretical value for 2 moles of water per mole of OND.

Dynamic vapor sorption (DVS) was then used to measure the weight loss of OND during an isotherm dehydration study. The DVS apparatus (Surface Measurement Systems, London, UK) was a commercially available water sorption apparatus, which allowed an OND sample to be weighed under defined temperature and humidity conditions. About 14 mg of OND was weighed onto an aluminum pan. The DVS apparatus was programmed to run from 0% to 90% relative humidity (RH) at increments of 10% RH and then again going from 90% back to 0% RH at decrements of 10% RH. The study was conducted at 25° C. and in triplicate. The accuracy of the DVS apparatus was ±1.0% for the RH and ±0.2° C. for the temperature.

Figure 10:
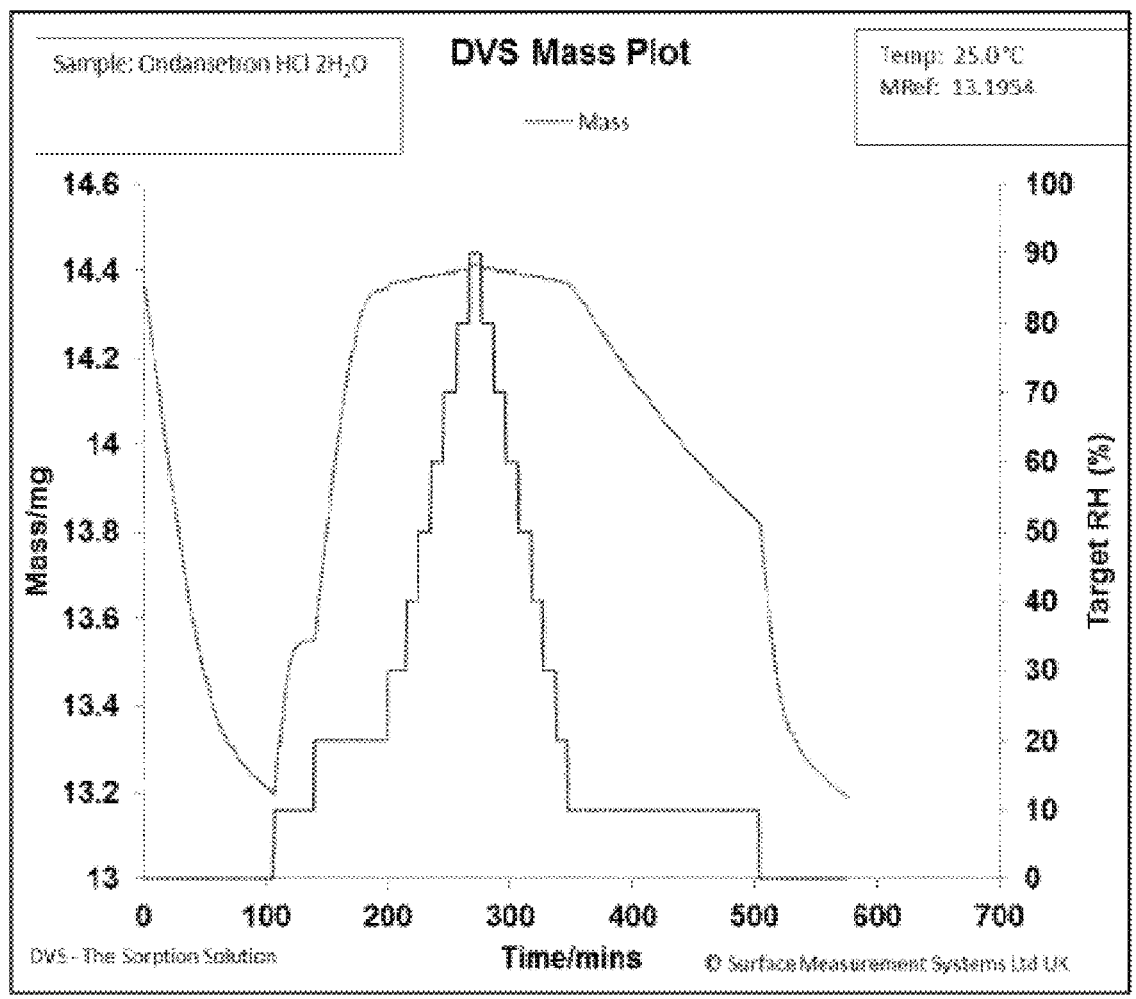
FIG. 10 is a mass plot of ondansetron HC1.2H20 generated by dynamic vapor sorption, as described in Example 2.
Figure 11:
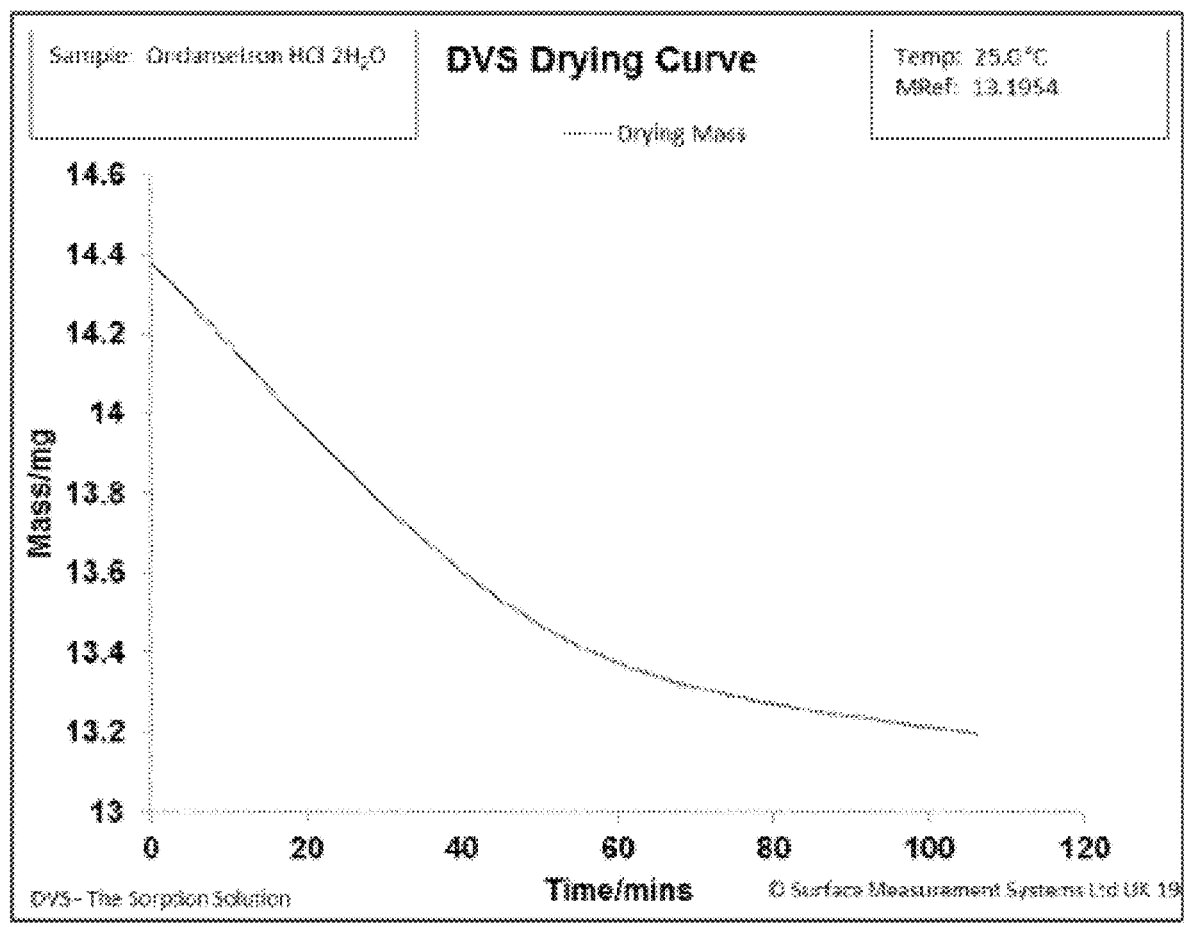
FIG. 11 is a drying curve of ondansetron HC1.2H20 generated by dynamic vapor sorption, as described in Example 2.

The DVS mass plot and the drying curve of OND are shown in FIGS. 10 and 11, respectively. The DVS mass plot showed a weight loss of 9.5% at 0% RH corresponding to the loss of two water molecules by dehydration of each OND molecule. As the RH increased from 0% to 10% and then to 20%, there was a 2.67% and 8.9% weight gain observed, respectively. There was only a very slight weight gain (from 8.9% to 9.2%) when the RH was increased beyond 20% up to 90%. Reversing the process, thereby decreasing RH from 90% to 20% only caused a slight weight loss for OND. At 10% RH, the dihydrate form of OND started to lose water and its weight decreased by up to 4.44%, corresponding to losing one water molecule per OND molecule. When humidity was further decreased, a rapid decrease in the water content of the OND was observed, indicating the loss of the second water molecule of the OND at or near 0% RH.

Hot-stage microscopy (HSM) was used to capture images at different stages of OND transformation. A glass slide with a sample of a small amount of OND dispersed in silicone oil was inserted into a hot-stage system (FTIR 600, Linkam Scientific Instruments, Surrey, UK). The OND sample was examined while being heated from 35° C. to 150° C. at a constant rate of 2° C./min. A camera-mounted optical microscope (Cary 620 IR, Agilent Technologies, Santa Clara, Calif., USA) equipped with a hot-stage was used to capture images at different stages of the OND transformation.

Figure 12:
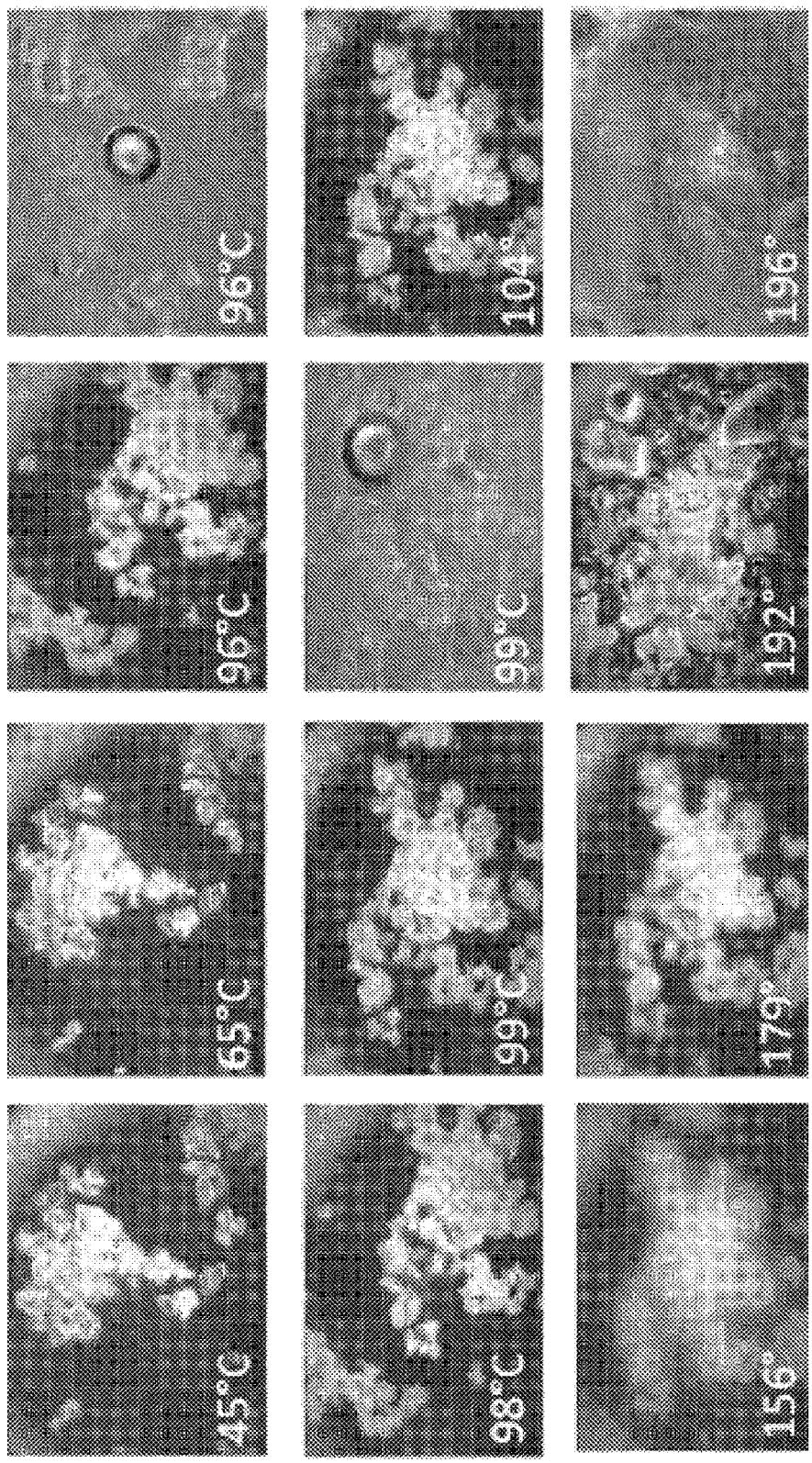
FIG. 12 illustrates hot stage microscopy images representing the thermal events associated with ondansetron HC1.2H20 dehydration.

HSM images are presented in FIG. 12. These images revealed that OND crystals started dehydration at a temperature of 90° C. and started melting at a temperature of 192° C. These HSM observations correlated well with the TGA thermogram where the dehydration event was observed at temperatures in the range of 60-105° C.

Inverse Gas chromatography-Surface Energy analysis (IGC-SEA) technique was used for characterizing surface and bulk properties of granules from twin screw dry granulation example above. The IGC-SEA is based on inverse gas chromatography (IGC) methodology and is a gas phase technique for characterizing surface and bulk properties of solid materials. The principles of IGC are simple, being the reverse of a conventional gas chromatographic (GC) experiment. A cylindrical column is uniformly packed with the solid material of interest, typically a powder, fibre, or film. A pulse of constant concentration of gas is then injected down the column at a fixed carrier gas flow rate, and the time taken for the pulse or concentration front to elute down the column is measured by a detector. A series of IGC measurements with different gas phase probe molecules then allows access to a wide range of phyisco-chemical properties of the solid sample.

The injected gas molecules passing over the material adsorb on the surface with a partition coefficient $k_s$:

$$K_s = v_n / w_s$$

Where vn is the net retention volume—the volume of carrier gas required to elute the injection through the column, and wS is the mass of the sample. Vn is a measure of how strongly the probe gas interacts with the solid sample and is the fundamental data obtained from an IGC experiment. From it a wide range of surface and bulk properties can be calculated. The injection manifold system can GENERATE accurate solvent pulse sizes across a large concentration range, resulting in isotherms at high and low sample surface coverages. This can allow for the determination of surface energy heterogeneity distributions. The surface energy distribution is the integration of the surface energy profile across the entire range at surface coverage and is analogous in principle to a particle size distribution. The above formulation was subjected to various barrel temperatures as per table below and at a screw speed of 100 rpm and a feed rate of 38 g/hr.

| Sample | Barrel temperature | | | | | |
|---|---|---|---|---|---|---|
| | ZONE 2 | Z3 | Z4 | Z5 | Z6 | Z7 |
| F1 | 50 | 50 | 60 | 70 | 60 | 50 |
| F2 | 70 | 70 | 80 | 90 | 80 | 70 |
| F2-F3 intermediate | 80 | 80 | 90 | 100 | 90 | 80 |
| F3 | 90 | 90 | 100 | 110 | 100 | 90 |
| F4 | 120 | 120 | 130 | 140 | 130 | 120 |
| F5 | 140 | 140 | 150 | 160 | 150 | 140 |

Figure 19:
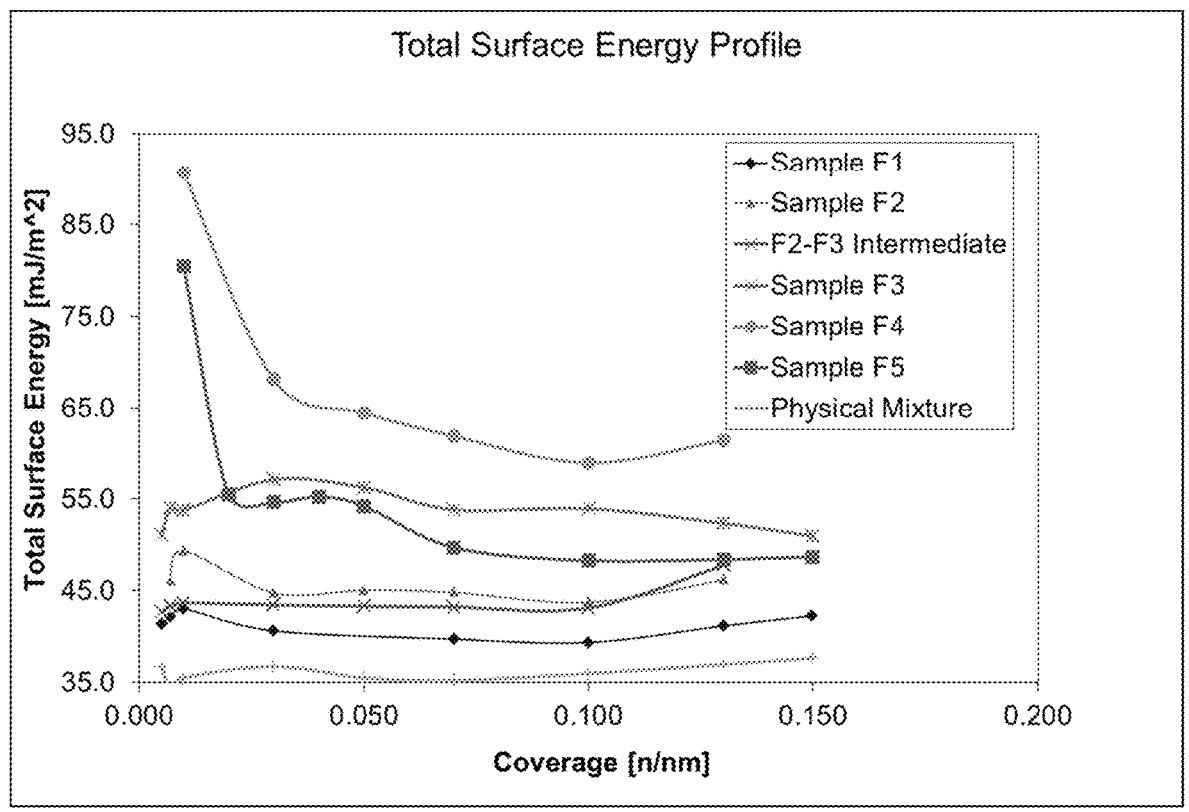
FIG. 19 illustrates the total surface energy profile of twin screw dry granulated formulations at various barrel temperatures, as described in Example 2.

The lower surface energy materials would be expected to have a lower degree of interaction with components in a blend. As per FIG. 19, physical mixture and samples F1 & F2 granulated at much lower temperatures show very low & constant surface energy profile over the surface coverage area. However, the total surface energy increases as the barrel temperature increases from sample F3 onwards. Sample F3 has a moderate surface energy profile as compared to high energy profile of samples F4 & F5. Samples F4 & F5 are also deemed as energetically anisotropic, i.e., they have regions of different surface energy. This is not favorable for granules as it can lead to the powder with varying bulk properties. However a stable & higher surface energy profile of sample F3 indicates that surface energy heterogeneity is much less than the other samples leading to granules with consistent physical properties. By principle, if a solid sample has high surface energy, its surface molecules are in a high-energy state and it is energetically favorable for them to form strong intermolecular bonds thus leading to better agglomeration of the powder. This indicates that the dry granulation formulations manufactured by twin screw technology has much higher energy than those created at lower shear values & temperatures.

Example 3: Extended Release Ondansetron (OND) Tablets

The materials used in this example were ondansetron HCl dihydrate purchased from Chemscene LLC (New Jersey, USA), hydroxypropyl cellulose (Klucel EF) from Ashland Specialty Ingredients (Wilmington, Del.), and ethyl cellulose (Ethocel Standard 10) from Dow Chemical Company. Fumaric acid and magnesium stearate were purchased from Spectrum Laboratory Products Inc. (Gardena, Calif.).

Differential scanning calorimetry (Diamond DSC, Perkin Elmer Life and Analytical Sciences, 710 Bridgeport Ave., Conn., USA) equipped with Pyris manager software (Shelton, Conn., USA) and Fourier transform infrared spectroscopy (FTIR, Agilent Technologies Cary 660, Santa Clara, Calif.) were used to study the compatibility of OND with various polymeric carriers in 1:1 ratio in a dry granulation process carried out in a twin-screw extruder to provide granules used to produce extended release tablets.

Samples were prepared by hermetically sealing approximately 3-5 mg of pure OND or powder mixture in aluminum pans, which were then heated over a temperature range of 40-250° C. at a linear heating rate of 10° C./min under an inert nitrogen atmosphere. An FTIR bench equipped with a MIRacle® attenuated total reflection (Pike Technologies, Madison, Wis.) was used to generate mid-infrared spectra in the range of 4000-650 cm−1, which was fitted with a single bounce diamond coated ZnSe internal reflection element.

Figure 13:
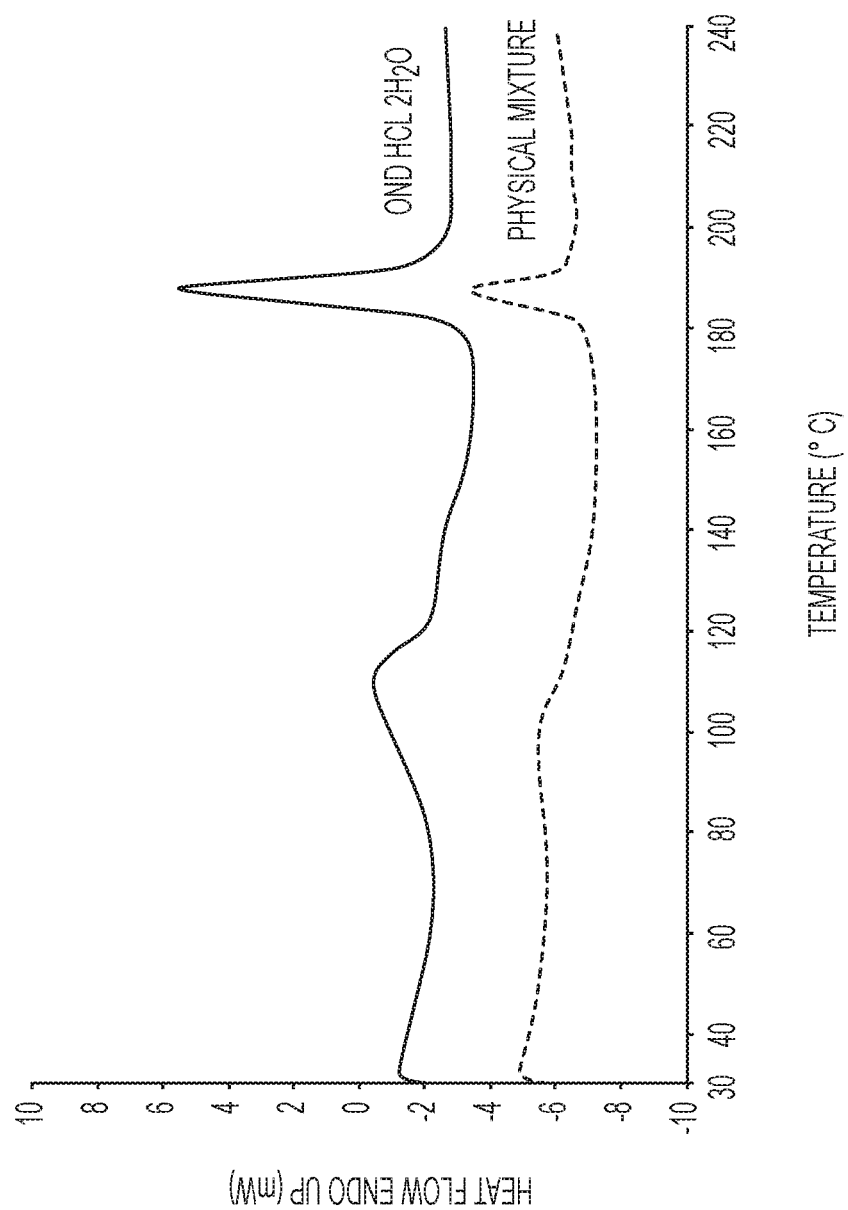
FIG. 13 illustrates DSC curves of pure ondansetron HC1.2H20 and the powder mixture of Example 3.

The selected DSC curves of the OND and powder mixture are shown in FIG. 13. The DSC curves show a typical melting point endothermic peak of pure OND in the range of 185.2-188.58° C. The DSC curves also indicate that OND was compatible with the tested polymeric carriers because there was no change in the glass transition temperature or melting endotherms when different polymeric carriers were used in the powder mixture. This observation was further confirmed by FTIR, which showed no change in the infrared spectrum of the OND when mixed with different polymeric carriers.

The dry granulation process was performed using the formulations and granulation parameters shown in Tables 10 and 11, respectively. Intragranular magnesium stearate was added to the powder mixture for producing the granules and extragranular magnesium stearate was added to the formed granules for producing the tablets. OND and polymeric carriers were passed through US mesh #35 (500 μM) in order to remove aggregates. Fumaric acid was added to the formulations prior to compression to increase the pH-dependent solubility of the OND. Magnesium stearate was also added to the formulations as a powder lubricant. Further, the powder mixture of OND (about 20 wt. %) and polymeric carriers (about 79%), with a minor amount of lubricant, was produced using a V-shell blender (GlobePharma, Maxiblend™ New Brunswick, N.J.) at 25 rpm for 20 min. Dry granulation was performed without an extrusion die block in a fully intermeshing co-rotating twin-screw extruder (11 mm Process 11™ Thermo Fisher Scientific) with modified screw configurations (FIG. 5). The powder mixture was fed to the extruder by a volumetric feeder and the zone adjacent to the feeder was not heated (Table 11).

Barrel temperatures for all screw barrel zones are shown in Table 11. The powder feed rate (g/min) and the screw speed (rpm) were each set at two levels, low and high. As soon as the twin-screw extruder reached a steady state, the granules were collected at the outlet of the extruder. The collected granules were stored in sealed aluminum pockets for further analysis.

TABLE 10

Granulation Formulations

| Formulations | OND (%) | EC (%) | HPC (%) | Fumaric acid (%) | Magnesium stearate (%) |
|---|---|---|---|---|---|
| A | 20% | 36.25% | 36.25% | 7.5% | 0.2% intragranular plus 0.3% extragranular |
| B | 20% | 37.5% | 37.5% | 5% | 0.2% intragranular plus 0.3% extragranular |
| C | 20% | 38.75% | 38.75% | 2.5% | 0.2% intragranular plus 0.3% extragranular |

TABLE 11

Screw barrel temperatures
Barrel Temperature (° C.)

| Feed Zone | Zone 2 | Zone 3 | Zone 4 | Zone 5 | Zone 6 | Zone 7 | Zone 8 | Discharge |
|---|---|---|---|---|---|---|---|---|
| N/A | 70 | 70 | 80 | 90 | 80 | 70 | 70 | 40 |

Different screw configurations (FIG. 5) were used in the twin-screw extruder to produce dry granules. Screw Configuration 1 resulted in about 20% granules and about 80% of fine powder, even with the screw barrel at a high barrel temperature. Screw Configuration 2 resulted in more granules and less fine powder. Screw Configuration 3 produced significant amounts of granulated particles and the granules had a rubbery texture, which was hard to break while passing through a sieve. Screw Configuration 2 produced the best quality granules and particle size distribution, with around 89% of the granules falling within the desired particle size range (500 μm-1.4 mm).

Figure 14:
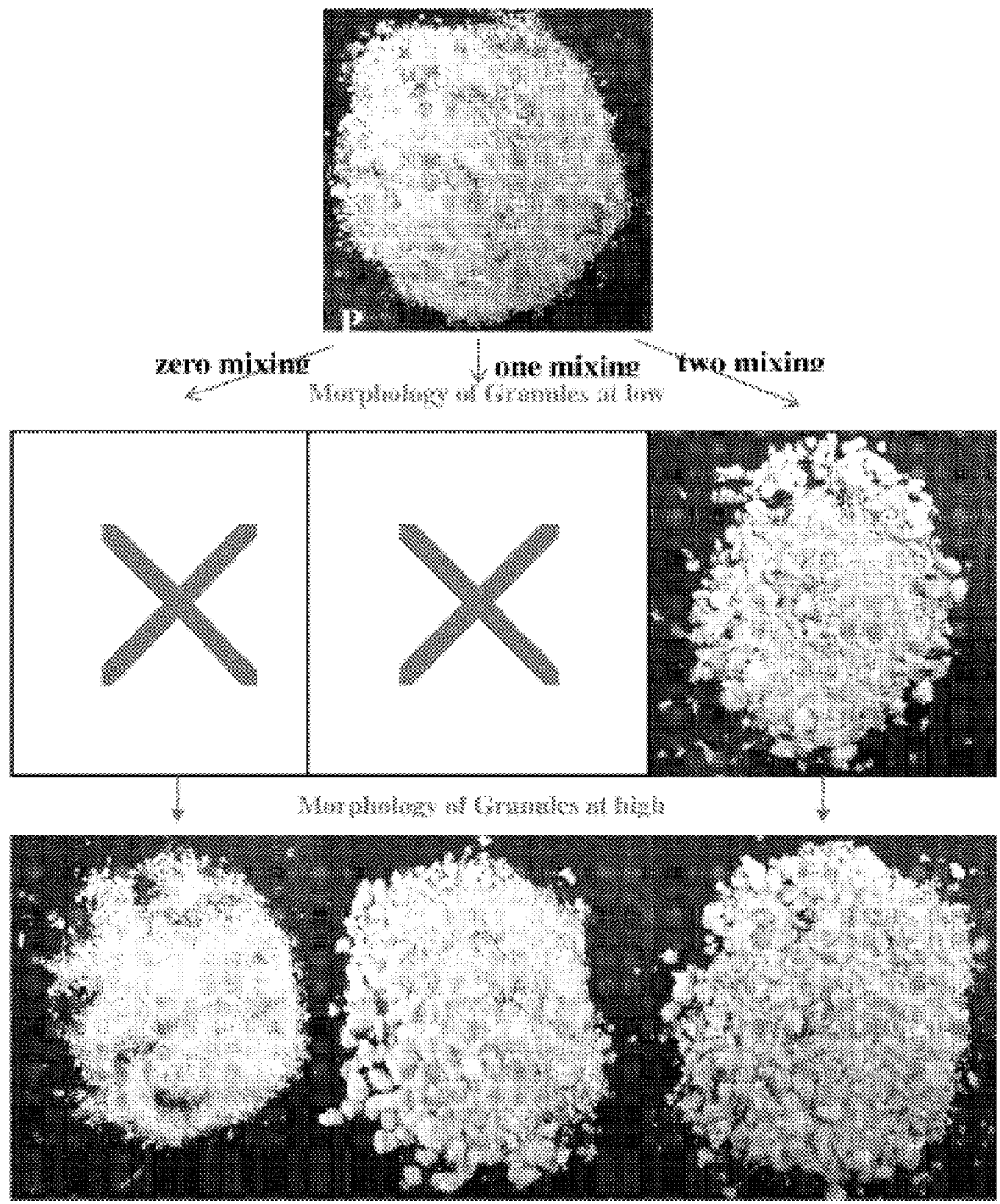
FIG. 14 illustrates digital images of a pre-granulation powder mixture and granulation products using different screw configurations and at different barrel temperatures, as described in Example 3.

Different barrel temperatures were used with the various screw configurations 1-3 for dry granulation of a powder mixture with OND and polymeric carrier. Digital images of the granules prepared with different screw configurations and at different barrel temperatures are shown in FIG. 14. It was observed that a barrel temperatures in the range of 70-90° C. showed promising results without melting of the polymers. Further, the screw configuration with one mixing element produced mostly medium sized granules. Therefore, a combination of screw configuration 2 and a barrel temperature in the range of 70-90° C. was selected for further testing.

Polymeric carriers were employed at either 1:1 or 3:1 ratios of EC to HPC. A 1:1 ratio of EC and HPC provided a larger percentage of medium sized granules and was selected for further tests.

The granules were compressed into tablets with or without addition of an organic acid. The tablets without organic acid were unable to release OND in intestinal pH media due to its weakly basic nature. An organic acid would solubilize OND in a high pH dissolution medium corresponding to an intestinal pH. Among citric acid, adipic acid and fumaric acid, fumaric acid showed the most promise as it was able to release 100% of the drug at an intestinal pH. Magnesium stearate was also added to the granules at 0.2% as a powder lubricant for the tableting step.

Ten batches of granules were made by the dry granulation process in a twin-screw extruder using 10 different granulation settings. Yields of the dry granulation process were found to be high (97-99%). Neither the polymeric carriers nor the OND melted during dry granulation using these parameters. No sticking material was observed inside the screw barrel walls or the screws.

The crystallinity of OND in the granules was compared to pure OND using a DSC curve for pure OND which showed a melting endothermic peak at 189° C. For all batches Z1-Z10, an endothermic peak was observed in the range of 185-191° C. Thus, the crystalline structure of OND was preserved in the granules.

The particle size distribution of the granules was studied using a sieve analysis method. Two USA standard test sieves, #35 (500 μm) and #14 (1.4 mm) were used and the amount of granules retained on each sieve was weighed. Three fractions were collected and weighed, one larger than 1.4 mm, a medium size between 1.4 mm and 500 μm and un-granulated fines with a size less than 500 μm. The percentile weight distribution was determined (Table 12). For tableting, the medium sized granules were the most important fraction and were used along with 10-15% fines in order to provide the desired compressibility. Thus, the dry granulation parameters were selected to obtain the maximum percentage of granules of medium size. For further testing, the production of granules having a size between 1.4 mm and 500 μm was selected as the sole dependent variable (response) in the $2^3$ factorial model,

TABLE 12

Characterization of Granules/Tablets

| Batch | Large granules (%) | Medium granules % | Fines % | Hausner's Ratio | Carr's Index | Angle of Repose | 100% Drug Release (h) |
|---|---|---|---|---|---|---|---|
| Z1 | 40.77381 | 53.21621 | 6.009985 | 1.09 | 8.69 | 34 | 6.5 |
| Z2 | 26.04511 | 65.20301 | 8.75188 | 1.22 | 18.18 | 36 | 6.5 |
| Z3 | 70.39839 | 24.6483 | 4.953304 | 1.13 | 11.53 | 33 | 7.5 |
| Z4 | 81.45596 | 14.66561 | 3.878434 | 1.08 | 8 | 43 | 7.5 |
| Z5 | 46.61275 | 48.99556 | 4.391686 | 1.13 | 11.53 | 30 | 9.5 |
| Z6 | 37.40889 | 57.97194 | 4.619169 | 1.13 | 11.53 | 31 | 10.5 |
| Z7 | 37.91596 | 57.76051 | 4.323537 | 1.13 | 11.53 | 36 | 9.5 |
| Z8 | 5.575453 | 89.6525 | 4.772045 | 1 | 0 | 25 | 15.5 |
| Z9 | 46.101 | 49.33976 | 4.559243 | 1.22 | 18.51 | 31 | 12.5 |
| Z10 | 28.5657 | 68.91675 | 2.517553 | 1.04 | 4 | 27 | 15.5 | where A, B and C are the screw speed, feed rate, and amount of fumaric acid added to the powder blend prior to extrusion, respectively. A positive or negative sign of the polynomial term indicates an increase or decrease in the effect on the granule size by the independent variables. All three factors had a significant effect on the granule size, with feed rate producing the most significant effect. An increase in feed rate caused a decrease in the percentage of medium sized granules. The highest percentage of medium size granules were obtained at lower feed rate.

Screw speed was also found to have a significant influence on granule size since increasing the screw speed from 25 to 100 rpm resulted in an increase in the percentage of medium sized granules regardless the amount of fumaric acid. Higher fumaric acid contents in the formulation gave a lower percentage of medium sized granules. Hence, the dry granulation process should be conducted at a low feed rate, high screw speed, and with a low amount of fumaric acid.

The bulk volume ($V_o$) of 5 g of granules was measured in a 10 ml of graduated glass cylinder. The bulk density ($\rho_b$) was calculated by the following equation:

$$\text{Bulk density } (\rho_b) = \frac{\text{amount of granules weighed (5 g)}}{\text{bulk volume } (V_o)} \quad \text{Eq. 2}$$

The graduated glass cylinder was tapped manually 100 times until no further reduction in the volume of the granules was observed. Tapped density ($\rho_t$) was calculated by using the following equation:

$$\text{Tapped density } (\rho_t) = \frac{\text{amount of granules weighed (5 g)}}{\text{tapped volume } (V_{100})} \quad \text{Eq. 3}$$

Carr's (compressibility) index (CI) and Hausner's ratio (HR) were calculated by the following equations:

$$CI = \frac{(P_t - P_b)}{P_t} \times 100 \quad \text{Eq. 4}$$

$$HR = \frac{P_t}{P_b} \quad \text{Eq. 5}$$

The angle of repose for the granules was determined by the funnel method. A funnel was placed above a horizontal plane surface on which a wax paper was placed. The accurately weighed granules were freely poured through the funnel onto the wax paper. The height of the funnel above the horizontal plane surface was adjusted in such a way that the tip of the formed cone of the granules just touched the tip of the funnel. The diameter and height of the cone were measured and the angle of repose (θ) was calculated by the following equation:

$$\text{Tan } (\theta) = \frac{h}{r} \quad \text{Eq. 6}$$

where, 'h' and 'r' are the height and radius of the formed cone of granules, respectively.

Flow properties of the granules were important to mixing, die filling and tableting of the granules, and thus may significantly affect dosage uniformity, content and tablet mechanical characteristics. A Hausner's ratio less than 1.25 or a Carr's index below 15 was considered an indication of good flowability. All of the batches Z1-Z10 had a Hausner's ratio value be:pw of 1.25 (Table 12). All the batches had a Carr's index value of less than 15 except batches Z2 and Z9 (Table 19). An angle of repose in the range of 25 to 30 indicated excellent flow properties. Batches Z5, Z8 and Z10 had an angle of repose of <30. Other batches showed angle of repose greater than 30 (Table 12).

Based on the $2^3$ factorial model, screw speed and feed rate were found to be the most significant factors affecting the flowability of the granules. A polynomial regression equation was used to represent the relationship between flowability and the granulation parameters.

$$\text{Angle of Repose} = +32.60 - 3.37*A + 2.63*B + 1.12*AB - 1.38*AC - 2.37*ABC \quad \text{Eq. 12}$$

Figure 15:
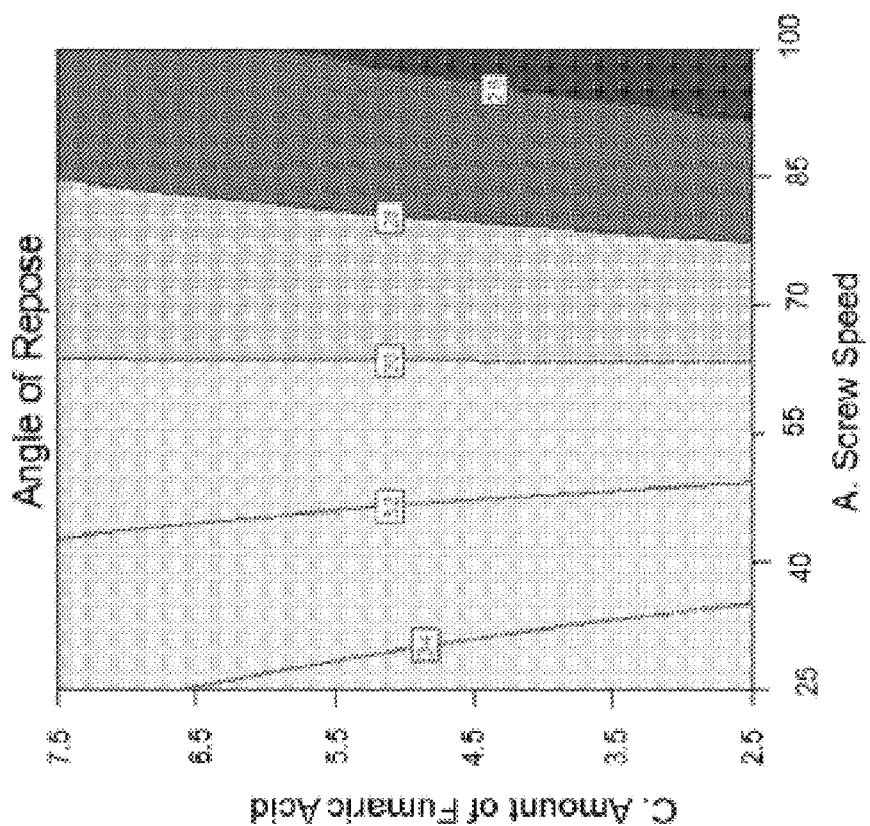
FIG. 15 illustrates contour plots and response surface graphs representing effects on the repose angle of granules of different granulation parameters, as described in Example 3.
Figure 15:
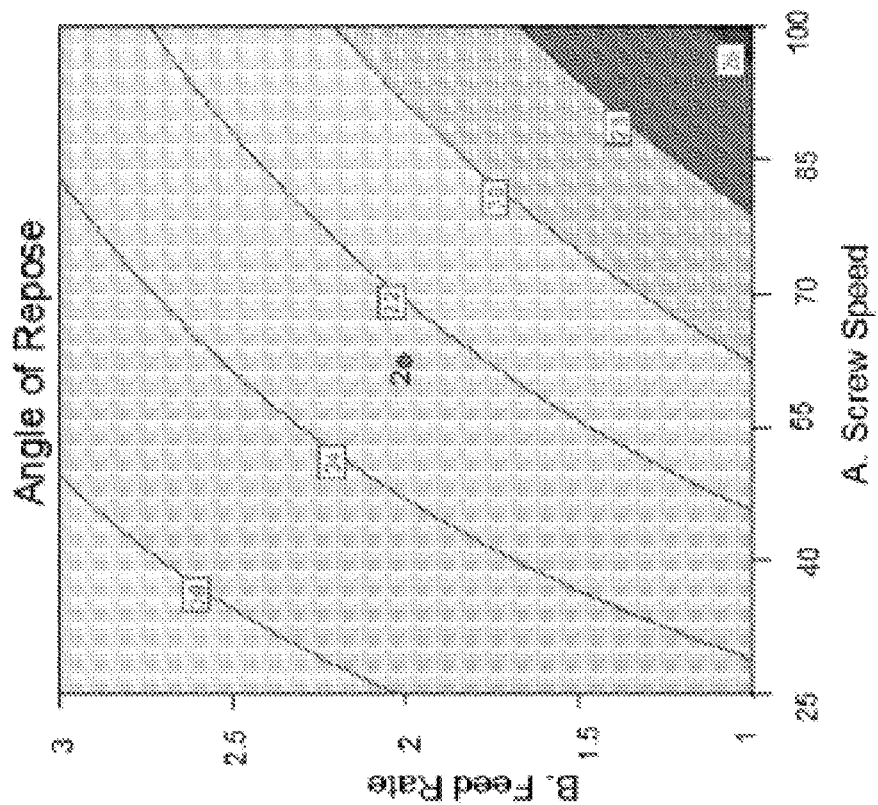
Figure 15:
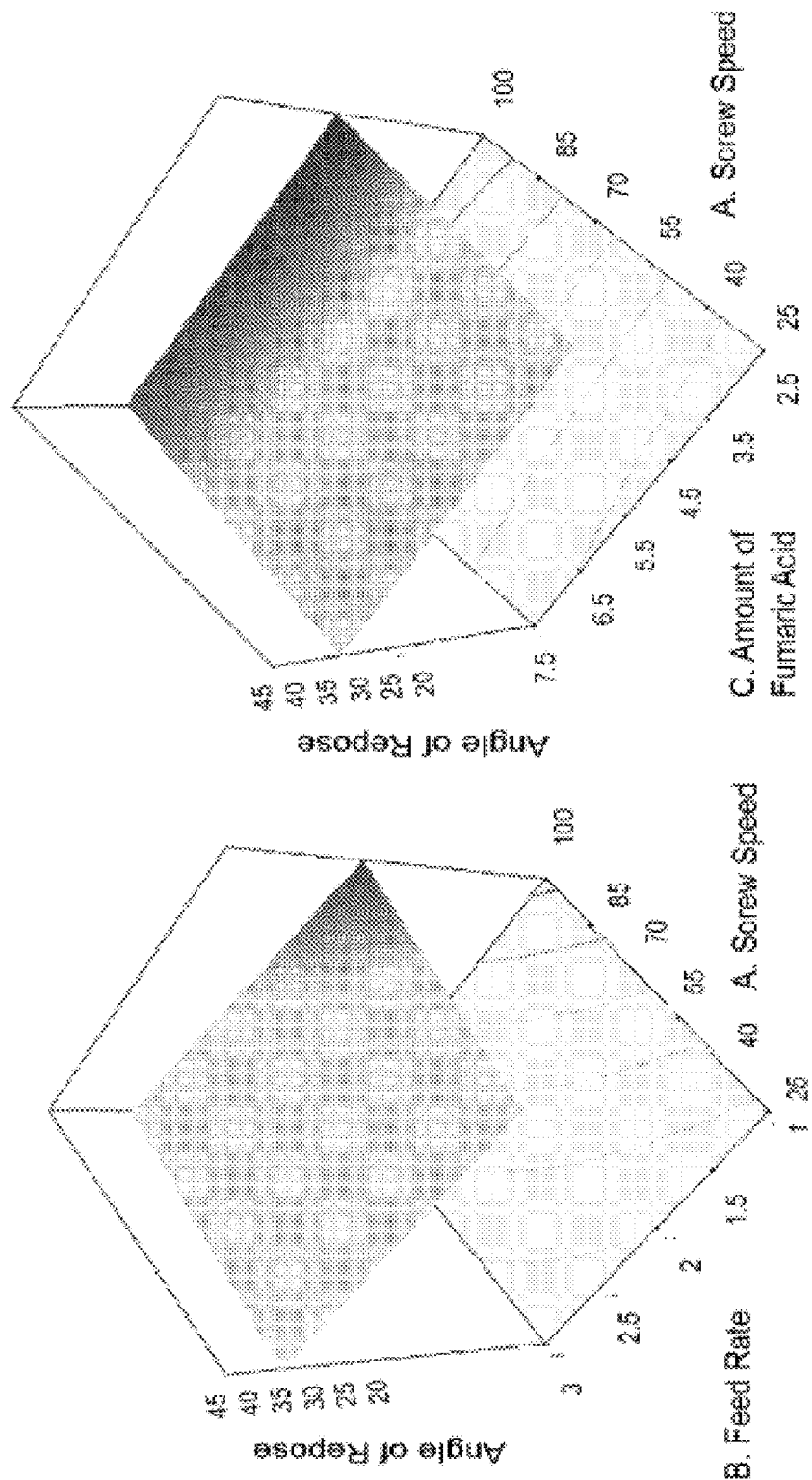

The screw speed (A) had the most significant effect on angle of repose of the granules. An increase in screw speed caused a decrease in the angle of repose. An increase in the feed rate (B) caused an increase in the angle of repose. These observations were well correlated with the particle size distributions of the granules. A high screw speed and low feed rate produced a higher percentage of medium sized granules, which had an improved flowability and a lower angle of repose. The correlation among these granulation parameters and the angle of repose of the granules is represented in a contour plot and a response surface graph (FIG. 15).

The true density of the granules was measured (n=3) with the help of a helium pycnometer (AccuPyc II 1340 Pycnometer, Micromeritics, USA). The surface area of the granules was determined (n=3) using a Gemini VII 2390

(Micromeritisc, USA). The true density and surface area of granules are presented in Table 13.

TABLE 13

True Density and Surface Area of Granules

| Batch | True density | Surface area (m2/g) |
|---|---|---|
| Z1 | 1.2419 ± 0.0013 | 0.2747 ± 0.0021 |
| Z2 | 1.2421 ± 0.0024 | 0.2015 ± 0.0046 |
| Z3 | 1.2490 ± 0.0014 | 0.2804 ± 0.0023 |
| Z4 | 1.2643 ± 0.0011 | 0.1717 ± 0.0023 |
| Z5 | 1.2801 ± 0.0012 | 0.3347 ± 0.0080 |
| Z6 | 1.2786 ± 0.0013 | 0.1278 ± 0.0034 |
| Z7 | 1.2227 ± 0.0017 | 0.3579 ± 0.0093 |
| Z8 | 1.2246 ± 0.0055 | 0.3239 ± 0.0079 |
| Z9 | 1.2163 ± 0.0014 | 0.3904 ± 0.0094 |
| Z10 | 1.2185 ± 0.0008 | 0.2565 ± 0.0061 |

The produced granules were mixed with 0.3% magnesium stearate just prior to being fed to a single punch tablet press (MCTMI, GlobePharma Inc., New Brunswick, N.J.), which used an 8 mm flat round punch at a compression force of 140 kg/cm. Ten tablets were randomly selected for testing with a Schleuniger-hardness tester. The thickness of the tablets was measured by a digital Vernier caliper (Montata). The tablet friability was determined using a dual scooping projection Vander Kamp friabilator (Vankel Industries Inc., Chatham, N.J.) rotating at speed of 25 rpm for 4 min. The tablet friability was expressed as the percentage weight loss of the tablets (weighed 6.5 g) after the dual scooping projection test.

For drug content uniformity, tablets were accurately weighed and the average weight was calculated. The tablets were ground with a mortar and pestle, and powder equivalent to 10 mg of OND was accurately weighed and dissolved in 0.1 N HCl. The absorbance was measured at $\lambda_{max}$ 305 nm using a UV-VIS Spectrophotometer and the percentage drug content was calculated using a calibration curve for OND.

It was observed that all of the produced tablets (from granules of batches Z1-Z10) had a uniform weight, thickness, and hardness. The average percentage deviation among tablets of each batch was less than ±5%. Hence all batches passed the test for uniformity of weight as per the USP official requirements.

Figure 16:
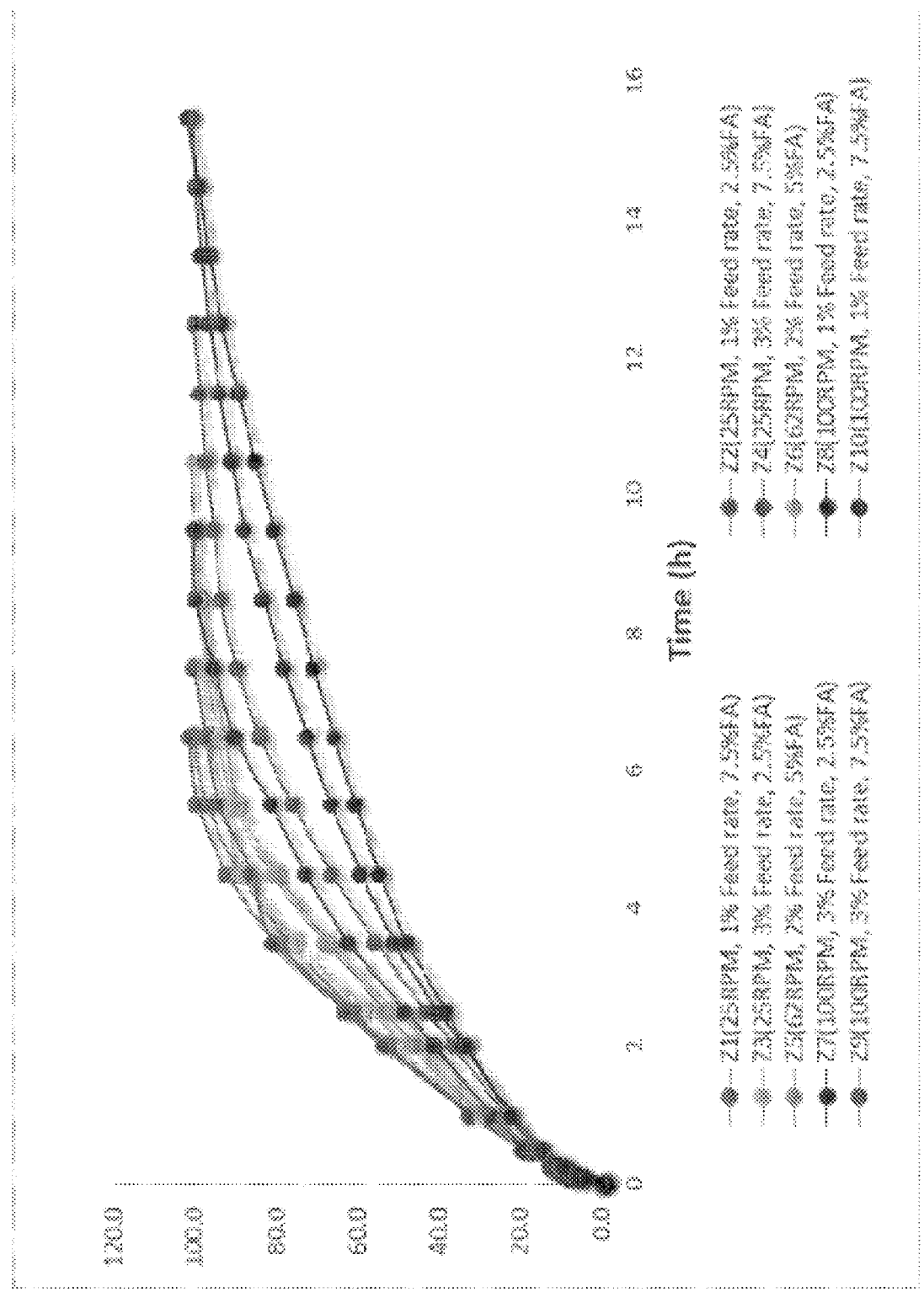
FIG. 16 illustrates a drug release profile of tablets made from granules produced using different granulation parameters, as described in Example 3.

In-vitro drug release from the tablets was measured using a USP dissolution apparatus type-II (Hanson SR8 Plus), set at a paddle speed of 50 rpm and equipped with UV-Vis probes (Rainbow dissolution monitor, PION). The UV spectra of the dissolution media were collected at $\lambda_{max}$ 305 nm every 2 min for the first 2 h and then every 25 min until 24 h. For the first 2 hours of the dissolution test, the dissolution media (pH 1.2) consisted of 700 ml of 0.1 N HCl with 1% sodium lauryl sulfate (SLS). At the 2 hour point, 200 ml of 0.2 M tribasic sodium phosphate (pH 12.5) with 1% SLS (maintained at 37±0.5° C.) was added to achieve and maintain a final pH of 6.8 for the dissolution media. This was for simulating transit of the tablet from the stomach (pH 1.2, first 2 hours) to the intestine (pH 6.8, next 22 hours). An in vitro drug release study was performed in triplicate and the mean % drug release was plotted versus the time in hours (FIG. 16).

The equation derived by employing a best fit mathematical model for the dissolution time based on the granulation parameters was:

Dissolution time=+10.10+3.13*$A$−0.88*$B$+0.38*$C$−1.38*$AB$+0.38*$BC$     Eq. 13

Figure 17:
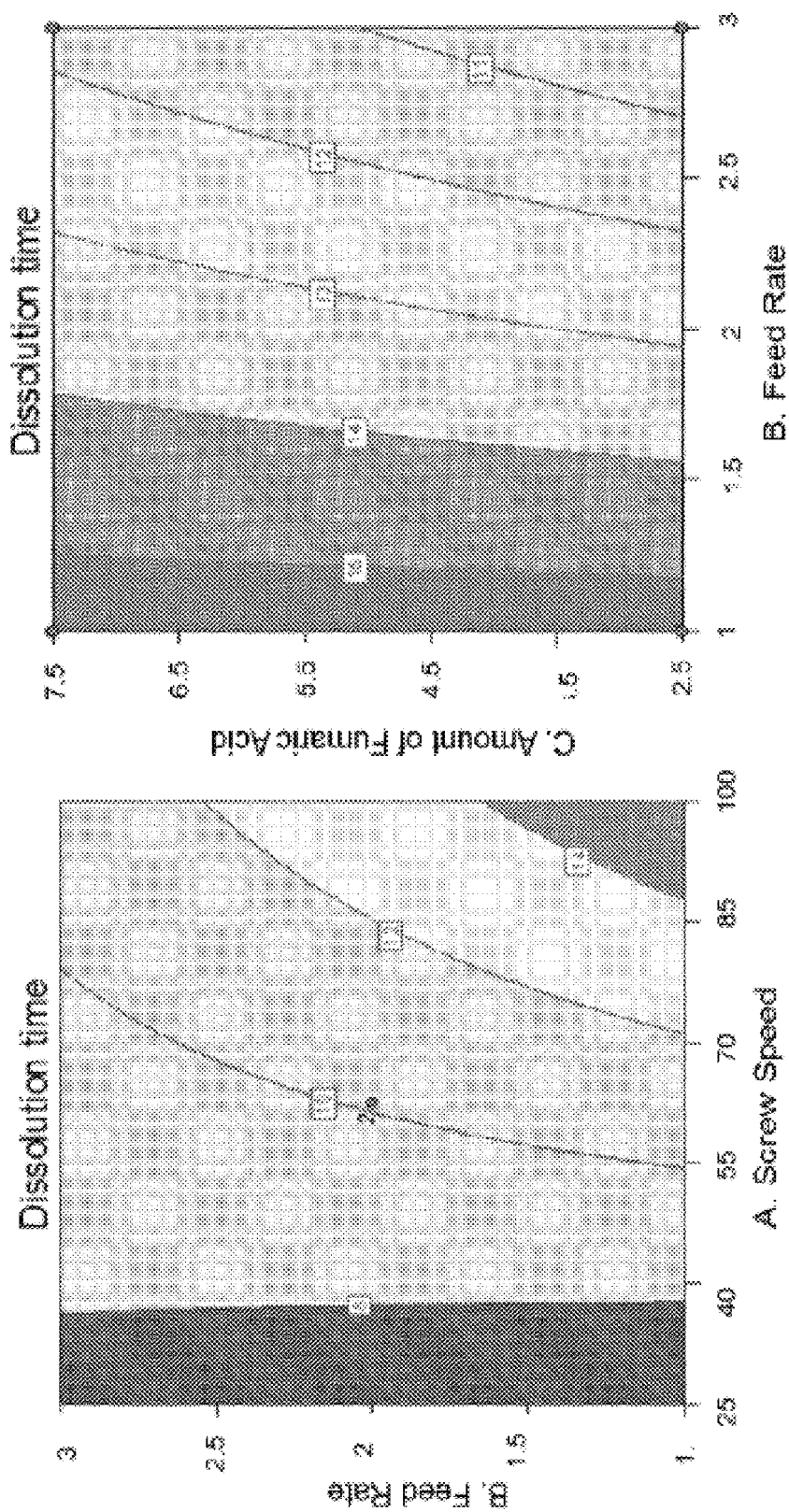
FIG. 17 illustrates contour plots and response surface graphs representing effects on the tablet dissolution time of different granulation parameters, as described in Example 3.
Figure 17:
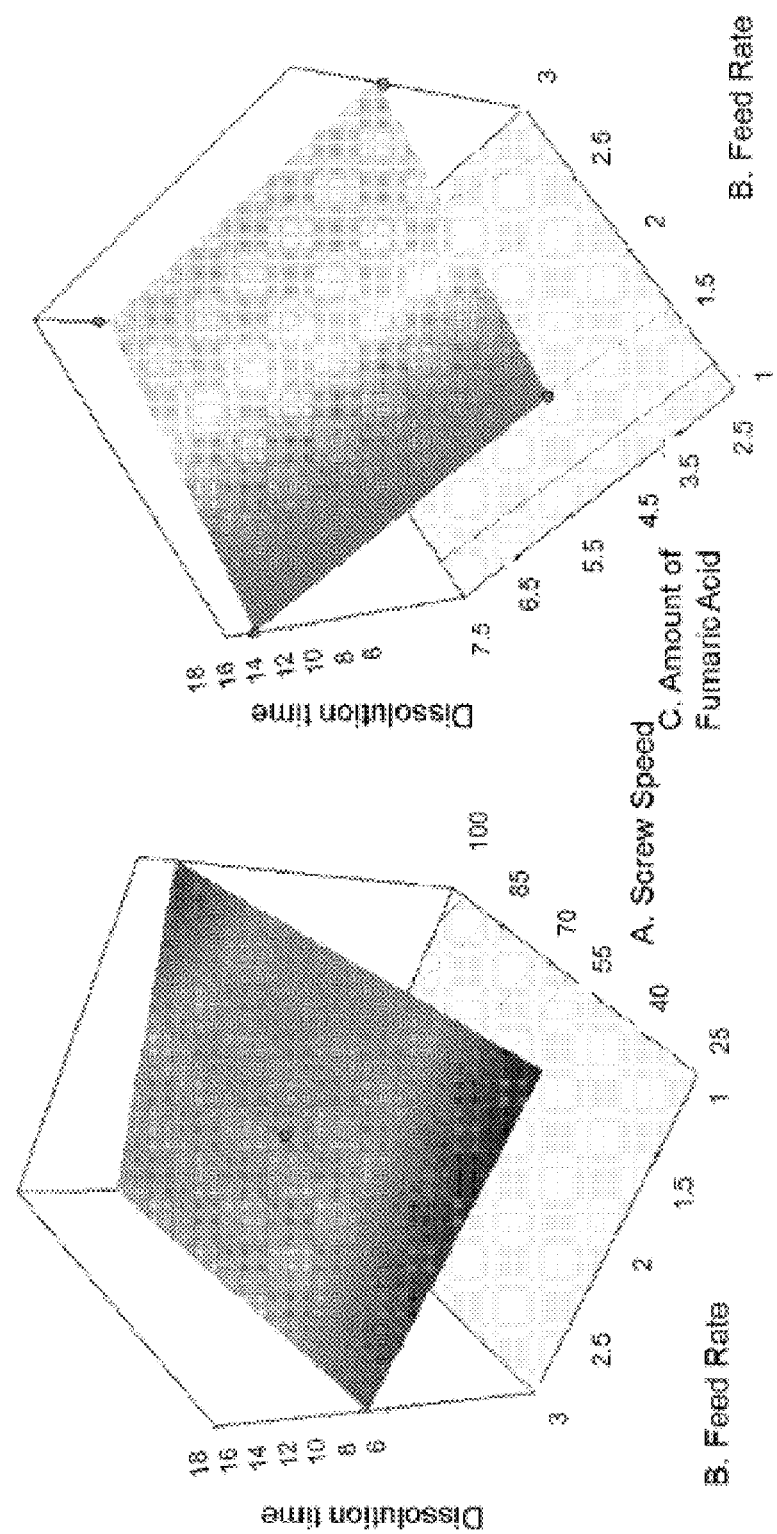

The screw speed (A) was the dominant factor affecting the drug release profile and tablets produced using a higher screw speed had a longer dissolution time. A negative interaction was observed for AB which had a significant negative effect on the dissolution time. Eq. 13 is presented in the form of a contour plot and response surface graph to visualize the effect of all changing independent variables on dissolution time (FIG. 17).

The in-vitro drug release dissolution data for 30 mg OND tablets was evaluated kinetically by using the following equations including zero-order, first-order, Higuchi and Korsmeyer-Peppas:

$$\text{Zero − order equation: } Q_t = Q_0 + K_0 t \quad \text{Eq. 7}$$

$$\text{First − order equation: } \log Q_t = \log Q_0 + \frac{K_1 t}{2.303} \quad \text{Eq. 8}$$

$$\text{Higuchi equation: } Q_t = K_H \sqrt{t} \quad \text{Eq. 9}$$

$$\text{Korsmeyer − Peppas equation: } \frac{Q_t}{Q_{00}} = K_{kp} t^n \quad \text{Eq. 10}$$

where, $Q_t$ is the amount of drug released in time t, $Q_O$ is the initial amount of the drug in the solution (most of the time $Q_0$32 0), $Q_{OO}$ is the amount of drug released after infinite time, $K_0$ is the zero order release rate constant, $K_1$ is the first order release rate constant, $K_H$ is the Higuchi diffusion rate constant, $K_{kp}$ is the kinetic release constant incorporating structural and geometrical characteristics of the tablets and 'n' is the diffusion coefficient indicating the drug release mechanism, which is dependent on the value of 'n'.

As shown in Table 14, kinetic modeling of the release data for all of the batches was fitted to the Korsmeyer-Peppas model. The diffusion coefficient (n) for tablets with granules from all of the batches were within the range of 0.59-0.72, indicating a non-Fickian diffusion mechanism and that drug release was governed by both diffusion and matrix erosion.

TABLE 14

Drug Release Kinetics

| Batch | Zero Order $R^2$ | First order $R^2$ | Higuchi $R^2$ | Korsmeyer peppas $R^2$ | n |
|---|---|---|---|---|---|
| Z1 | 0.9509 | 0.9444 | 0.991 | 0.9995 | 0.75 |
| Z2 | 0.9481 | 0.878 | 0.9878 | 0.999 | 0.72 |
| Z3 | 0.9342 | 0.9708 | 0.9818 | 0.9993 | 0.69 |
| Z4 | 0.9139 | 0.9808 | 0.979 | 0.9983 | 0.70 |
| Z5 | 0.9168 | 0.8568 | 0.9822 | 0.9993 | 0.63 |
| Z6 | 0.894 | 0.9066 | 0.9777 | 0.9973 | 0.62 |
| Z7 | 0.947 | 0.8014 | 0.9843 | 0.9985 | 0.58 |
| Z8 | 0.919 | 0.8323 | 0.9926 | 0.9982 | 0.59 |
| Z9 | 0.9151 | 0.9754 | 0.9761 | 0.9986 | 0.63 |
| Z10 | 0.9433 | 0.9011 | 0.9988 | 0.9997 | 0.62 |

Figure 18:
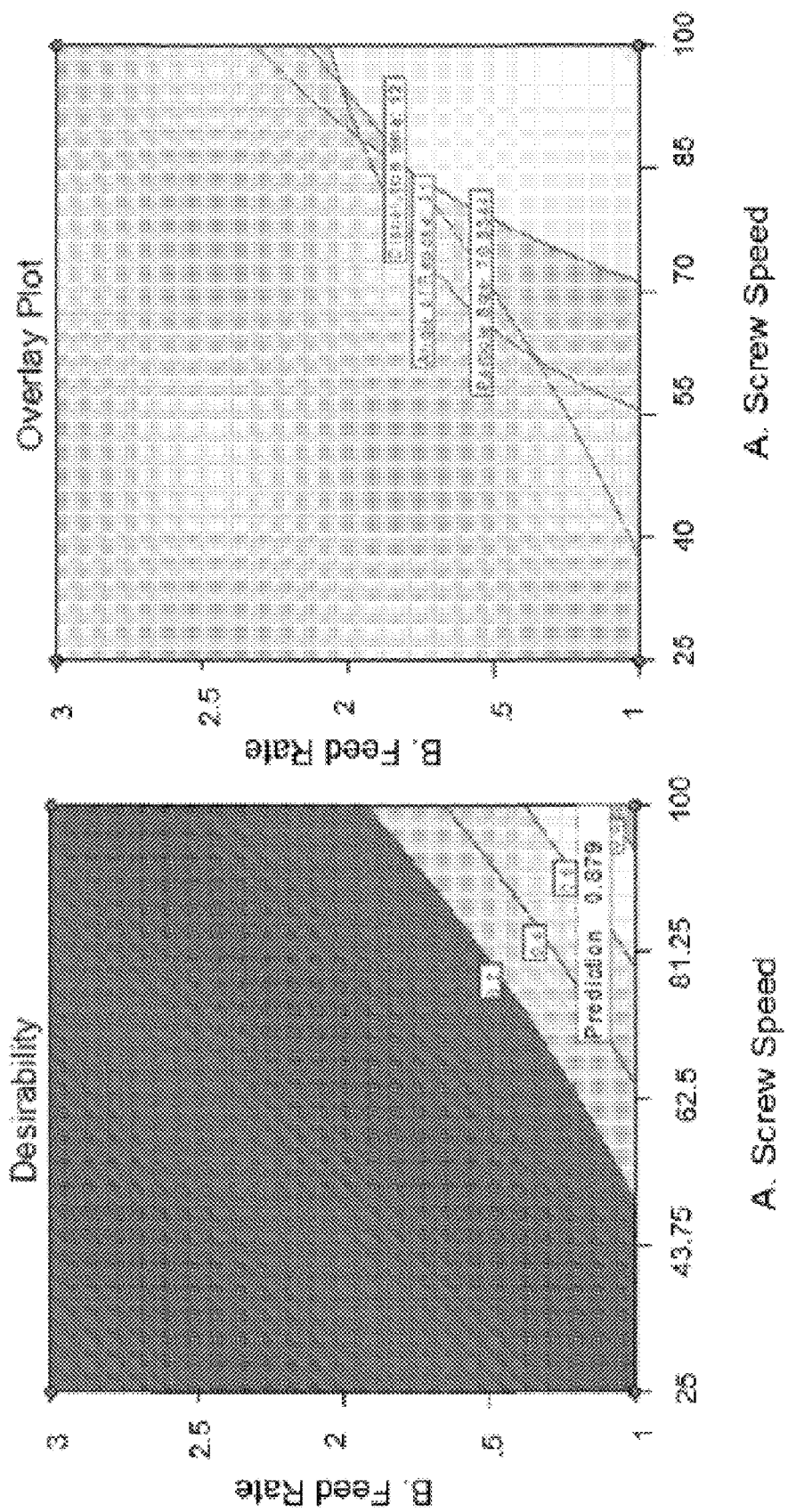
FIG. 18 illustrates a desirability plot and an overlay plot representing a selected feed rate and screw speed using a Quality by Design approach, as described in Example 3.

To achieve the combination of a high percentage of medium sized granules and the desired dissolution time required for attaining complete and extended drug release from the tablets, with a low angle of repose for the granules, a desirability plot was generated to understand the relationship between granulation parameters and the quality values (FIG. 18). Specifically, the produced granules should have good flow properties (a lower angle of repose with value within 25-31), a higher percentage of medium sized granules (70-90%) and more time should be required for dissolution of the dosage (a release time of 12-16 hours). The calculated desirability value for the batch Z8 is 0.880 which indicated suitability of the designed factorial model.

This application discloses several numerical ranges in the text and figures. The numerical ranges disclosed inherently support any range or value within the disclosed numerical ranges, including the endpoints, even though a precise range limitation is not stated verbatim in the specification because this disclosure can be practiced throughout the disclosed numerical ranges.

It is to be understood, however, that even though numerous characteristics and advantages of the present disclosure have been set forth in the foregoing description, together with details of the structure and function of the disclosure, the disclosure is illustrative only, and changes may be made in detail, especially in matters of shape, size and arrangement of parts within the principles of the disclosure to the full extent indicated by the broad general meanings of the terms in which the appended claims are expressed. Finally, the entire disclosure of the patents and publications referred in this application are hereby incorporated herein by reference.

What is claimed is:

1. A dry granulation method of producing granules comprising:
   mixing a first powder comprising at least one active ingredient and a second powder comprising at least one carrier to form a powder mixture;
   feeding the powder mixture to a twin-screw extruder without a solvent, liquid binder, or meltable binder;
   kneading the powder mixture in a heated screw barrel of the twin-screw extruder, wherein all temperatures along a length of the screw barrel are below a melting point of the at least one active ingredient and below a melting point or a glass transition temperature of the at least one carrier to form a kneaded powder mixture; and
   extruding the kneaded powder mixture to form the granules.

2. The method of claim 1, wherein the twin-screw extruder comprises two screws that are fully intermeshing, co-rotating screws.

3. The method of claim 1, wherein a barrel temperature at one location along a length of the screw barrel is different from a barrel temperature at another location along the length of the screw barrel.

4. The method of claim 1, wherein a first zone closest to an outlet of the screw barrel has a lower barrel temperature than a second zone at a center portion along the length of the screw barrel.

5. The method of claim 1, wherein all temperatures along the length of the screw barrel are between about 50-100° C.

6. The method of claim 1, wherein the twin-screw extruder does not have a die block for extruding the granules.

7. The method of claim 1, wherein the powder mixture further comprises a lubricant.

8. The method of claim 7, wherein the lubricant is added to the powder mixture before kneading the powder mixture.

9. The method of claim 7, wherein the lubricant comprises about 0.01-1 wt % the powder mixture.

10. The method of claim 7, wherein the lubricant is selected from the group consisting of magnesium stearate, zinc stearate, lithium stearate, calcium stearate, aluminum stearate, sodium stearyl fumarate, talc, glyceryl behenate, and colloidal silicon dioxide.

11. The method of claim 1, wherein the at least one active ingredient is selected from the group consisting of heat-sensitive active pharmaceutical ingredients, dehydration-sensitive active pharmaceutical ingredients, poorly-compressible active pharmaceutical ingredients, and high-dosage active pharmaceutical ingredients.

12. The method of claim 1, wherein all temperatures along the length of the screw barrel are below a melting point or a glass transition temperature of all components in the powder mixture.

13. The method of claim 1, wherein the melting point or the glass transition temperature of the at least one carrier is lower than the melting point of the at least one active ingredient.

14. The method of claim 1, wherein the powder mixture comprises two or more polymeric carriers.

15. The method of claim 1, wherein the at least one carrier is selected from the group consisting of polysaccharides, povidones, acrylates, celluloses and polyols.

16. The method of claim 1, wherein the at least one carrier is selected from the group consisting of homopolymers and copolymers of N-vinyl pyrrolidone, copolymers of N-vinyl pyrrolidone and vinyl acetate or vinyl propionate; cellulose esters and cellulose ethers, hydroxyalkylcelluloses, hydroxyalkylalkylcelluloses, cellulose phthalates, cellulose succinates; polyethylene oxide, polypropylene oxide, copolymers of ethylene oxide and propylene oxide; polyacrylates, polymethacrylates, polyacrylamides; vinyl acetate polymers, polyvinyl alcohol, oligo- and polysaccharidesand mixtures of one or more thereof.

17. The method of claim 1, wherein the at least one carrier is selected from the group consisting of hydroxylpropylcellulose, ethylcellulose, carboxymethylcellulose, hydroxyethylcellulose, methylcellulose, ethylhydroxyethylcellulose, hydroxyethylmethylcellulose, hydrophobically modified hydroxyethylcellulose, hydrophobically modified ethylhydroxyethylcellulose, carboxymethylhydroxyethylcellulose, and carboxymethyl hydrophobically modified hydroxyethylcellulose.

18. The method of claim 1, wherein the at least one carrier is a polymeric carrier having a molecular weight in a range of about 2,000-2,000,000 Daltons.

19. The method of claim 1, wherein the powder mixture further comprises at least one of a plasticizer, binder, filler, disintegrant, or organic acid.

20. The method of claim 1, wherein the powder mixture further comprises an organic acid.

21. The method of claim 1, wherein a screw speed of the twin-screw extruder is less than about 200 rpm.

22. The method of claim 1, wherein a feed rate into the twin-screw extruder is less than about 400 g/hr.

23. The method of claim 1, wherein the granules have an angle of repose of less than or equal to about 30.

24. The method of claim 1, wherein the granules have a compressibility index of about 10-30.

25. The method of claim 1, wherein the granules have a Hausner ratio of less than about 1.25.

26. The method of claim 1, wherein the granules have a true density of about 1.15-1.35.

27. The method of claim 1, wherein the granules have a surface area of about 0.05-0.45.

28. The method of claim 1, further comprising pressing the granules into a tablet.

29. The method of claim 28, wherein the tablet has a hardness of about 5-20 kp.

30. The method of claim 28, wherein the tablet has a friability of less than about 0.5%.

* * * * *